United States Patent
Pompon et al.

(10) Patent No.: US 10,066,234 B2
(45) Date of Patent: Sep. 4, 2018

(54) YEASTS MODIFIED TO USE CARBON DIOXIDE

(71) Applicants: Institut National De La Recherche Agronomique, Paris (FR); Institut National Des Sciences Appliquees De Toulouse, Toulouse (FR); Centre National De La Recherche Scientifique, Paris (FR)

(72) Inventors: Denis Pompon, Pechabou (FR); Frederic Paques, Clermont-Ferrand (FR); Julie Lesage, Belberaud (FR); Stephane Guillouet, Vallegue (FR); Florence Bonnot, Saix (FR); Jillian Marc, Toulouse (FR); Nathalie Gorret, Vallegue (FR); Carine Bideaux, Le Vernet (FR); Christel Boutonnet, Pins Justaret (FR)

(73) Assignees: Institut National de la Recherche Agronomique, Paris (FR); Institut National Des Sciences Appliquees De Toulouse, Toulouse (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 15/111,410

(22) PCT Filed: Jan. 16, 2015

(86) PCT No.: PCT/IB2015/050346
§ 371 (c)(1),
(2) Date: Jul. 13, 2016

(87) PCT Pub. No.: WO2015/107496
PCT Pub. Date: Jul. 23, 2015

(65) Prior Publication Data
US 2017/0002368 A1    Jan. 5, 2017

(30) Foreign Application Priority Data

Jan. 16, 2014   (FR) ...................................... 14 50349

(51) Int. Cl.
*C12N 9/88*   (2006.01)
*C12N 15/81*  (2006.01)
*C12N 9/12*   (2006.01)
*C07K 14/195* (2006.01)

(52) U.S. Cl.
CPC ............ *C12N 15/81* (2013.01); *C07K 14/195* (2013.01); *C12N 9/1205* (2013.01); *C12N 9/88* (2013.01); *C12Y 207/01019* (2013.01); *C12Y 401/01039* (2013.01); *C12N 2830/002* (2013.01); *Y02E 50/17* (2013.01)

(58) Field of Classification Search
None
See application file for complete search history.

(56) References Cited

FOREIGN PATENT DOCUMENTS

| WO | WO-2008/028019 A1 | 3/2008 |
| WO | WO-2008/135206 A2 | 11/2008 |
| WO | WO-2009/036095 A1 | 3/2009 |
| WO | WO-2013/066848 A1 | 5/2013 |

OTHER PUBLICATIONS

Bracher et al "Crystal Structure of a Chaperone-Bound Assembly Intermediate of Form I Rubisco" Nature Structural & Molecular Biology vol. 18, pp. 875-881, 2011.
Chang "Mechanisms of De Novo Multi-Domain Protein Folding in Bacteria and Eukaryotes" Dissertation zur Erlangung des Doktorgrades der Fakultat fur Chemie und Pharmazie der Ludwig-Maximilians-Universitat Munchen, 2006.
Chari et al "Cellular Strategies for the Assembly of Molecular Machines" Trends in Biochemical Sciences vol. 35, pp. 676-683, 2010.
Goloubinoff et al "GroE Heat-Shock Proteins Promote Assembly of Foreign Prokaryotic Ribulose Bisphosphate Carboxylase Oligomers in *Escherichia coli*" Nature vol. 337, pp. 44-47, 1989.
Guadalupe-Medina et al "Carbon Dioxide Fixation by Calvin-Cycle Enzymes Improves Ethanol Yield in Yeast" Biotechnology for Biofuels vol. 6, pp. 1-12, 2013.
Liu et al "Coupled Chaperone Action in Folding and Assembly of Hexadecameric Rubisco" Nature vol. 463, pp. 197-204, 2010.

*Primary Examiner* — James S Ketter
(74) *Attorney, Agent, or Firm* — Cesari and McKenna, LLP

(57) ABSTRACT

The invention relates to yeast cells modified to express a functional type I RuBisCO enzyme, and a class II phosphoribulokinase. The expression of these enzymes recreates a Calvin cycle in said yeasts in order to enable the yeasts to use carbon dioxide.

23 Claims, 12 Drawing Sheets

Figure 1:
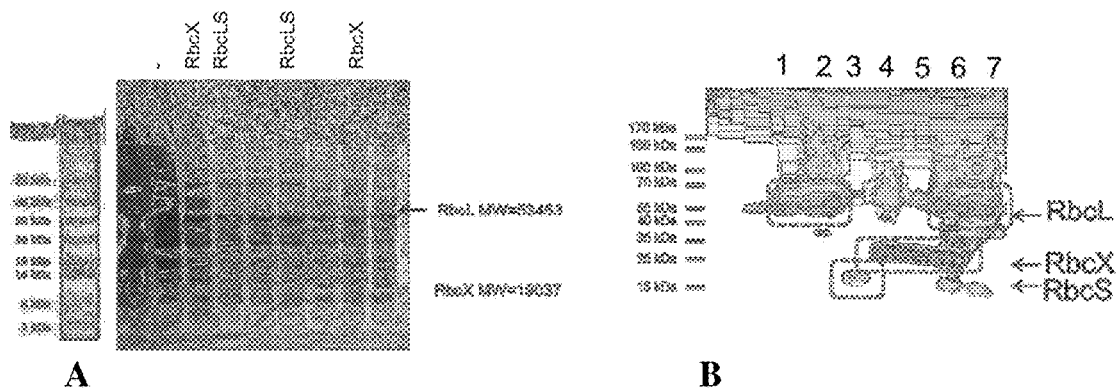

Specification includes a Sequence Listing.

SEQUENCE LISTING

```
<160> NUMBER OF SEQ ID NOS: 11

<210> SEQ ID NO 1
<211> LENGTH: 1537
<212> TYPE: DNA
<213> ORGANISM: Synechococcus elongatus
<220> FEATURE:
<221> NAME/KEY: misc_feature
<222> LOCATION: (1)..(64)
<223> OTHER INFORMATION: recombination arms
<220> FEATURE:
<221> NAME/KEY: misc_feature
<222> LOCATION: (65)..(1483)
<223> OTHER INFORMATION: ORF for RbcL
<220> FEATURE:
<221> NAME/KEY: misc_feature
<222> LOCATION: (1485)..(1537)
<223> OTHER INFORMATION: recombination arms
```

<400> SEQUENCE: 1

```
actagtttac ttcttgctca ttagaaagaa agcatagcaa tctaatctaa gttttaatta        60
caaaatgcct aagactcaat cggctgccgg ttacaaggca ggtgtaaaag attacaaact       120
aacttattat actccagatt atacacccaa agacactgac ttactagccg cctttcgctt       180
ttcgccccag ccaggtgttc cagctgatga agctggtgct gctatcgctg ctgaatcttc       240
tactggtact tggactactg tttggactga tttattaact gatatggaca gatacaaagg       300
caaatgttac catattgaac cggttcaagg tgaggaaaat tcttattttg cttttatcgc       360
atacctcta gatctttttg aagagggttc tgttactaat atcttaactt ctatcgtcgg       420
taatgtcttt ggctttaagg ccattcgtag cctacgtctt gaagacatca ggtttccagt       480
tgctttagtt aaaactttc aaggtccacc acatggtatc aagtagaaac gggatctttt       540
aaataaatat ggcagaccga tgctcgggtg cacgattaag ccgaagctcg ggcttctgc        600
taaaaattat ggtagagctg tttatgaatg tttacgtggt ggtttagatt ttactaaaga       660
tgatgaaaat atcaattctc aaccgttcca gcgttggcgg gaccgattcc tctttgtggc       720
cgacgcgatc cataaatctc aagctgaaac tggtgaaatc aaaggtcatt atttaaatgt       780
aacggcgcct acatgtgaag aaatgatgaa gcgagcagaa tttgctaagg aactaggtat       840
gcctatcatc atgcatgatt ttttaactgc tggttttact gctaatacta ctttagctaa       900
atggtgccgg acaatggag tcctattaca tatccatcgt gccatgcacg cggtcattga       960
tcgtcaaagg aatcatggta tccatttag agttttagct aaatgtttaa gattatctgg      1020
tggtgatcat ttacattctg gtactgtcgt gggaaagctt gagggtgaca aggcatctac      1080
attaggtttt gttgatttaa tgagagaaga tcatatcgaa gctgatagat ctagaggtgt      1140
tttttttact caagactggg cgtcgatgcc ggggtgctc ccagttgctt ctggtggtat      1200
ccatgtttgg cacatgccgg cgttagttga aatctttggt gatgattctg ttttacaatt      1260
tggtggtggt actttaggtc atccatgggg taatgcacca ggtgctactg ctaatagagt      1320
tgctttagaa gcttgtgttc aagctagaaa tgaaggtaga gatttatata gagagggtgg      1380
tgatattta agggaagcag gtaaatggtc gcctgaactg gcagccgccc tcgatttatg      1440
gaaagaaatc aaatttgaat ttgaaactat ggataaatta taagaattcg cggggatct       1500
cccatgtctc tactggtggt ggtgcttctt tggtacc                              1537
```

<210> SEQ ID NO 2
<211> LENGTH: 454
<212> TYPE: DNA
<213> ORGANISM: Synechococcus elongatus
<220> FEATURE:
<221> NAME/KEY: misc_feature
<222> LOCATION: (1)..(64)
<223> OTHER INFORMATION: recombination arms
<220> FEATURE:
<221> NAME/KEY: misc_feature
<222> LOCATION: (65)..(400)
<223> OTHER INFORMATION: ORF for Rbcs
<220> FEATURE:
<221> NAME/KEY: misc_feature
<222> LOCATION: (401)..(454)
<223> OTHER INFORMATION: recombination arms

<400> SEQUENCE: 2

```
actagtttac ttcttgctca ttagaaagaa agcatagcaa tctaatctaa gttttaatta        60
caaaatgtca atgaagacgc tccctaaaga aaggagattt gaaacgtttt catatctgcc       120
```

-continued

```
ccctctctct gatagacaaa tcgctgctca aatcgaatat atgatcgaac aaggttttca      180
tccattaatc gaatttaatg aacattctaa tccagaagaa ttttattgga ctatgtggaa      240
gctccctctt tttgattgta aatctcctca acaggtttta gatgaagtga gagagtgtag      300
atctgaatat ggtgattgtt atatcagagt tgctggtttt gataatatca acaatgtca       360 aactgtttct tttatcgttc atagacctgg aagatactaa gaattcgcgg gggatctccc      420
atgtctctac tggtggtggt gcttctttgg tacc                                  454

<210> SEQ ID NO 3
<211> LENGTH: 604
<212> TYPE: DNA
<213> ORGANISM: Synechococcus elongatus
<220> FEATURE:
<221> NAME/KEY: misc_feature
<222> LOCATION: (1)..(64)
<223> OTHER INFORMATION: recombination arms
<220> FEATURE:
<221> NAME/KEY: misc_feature
<222> LOCATION: (65)..(550)
<223> OTHER INFORMATION: ORF for RbcX
<220> FEATURE:
<221> NAME/KEY: misc_feature
<222> LOCATION: (551)..(604)
<223> OTHER INFORMATION: recombination arms

<400> SEQUENCE: 3
actagtttac ttcttgctca ttagaaagaa agcatagcaa tctaatctaa gttttaatta       60
caaaatgcaa tttatgggta ctgcttctag gatggcgtcg acgcaacggg ccaagcctat      120
ggagatgccg aggattagcc gtgatactgc tagaatgtta gttaattatt taacttatca      180
agctgtttgt gttatcagag atcaattagc tgaaactaat ccagctggtg cctatagatt      240
acaagttttt tctgctgaat tttcttttca agatggtgaa gcttatttag ctgctttatt      300
aaatcatgat agagaattag gactaagggt gatgacggta agggaacatt tagctgaaca      360
tattctagat tatcttccag aaatgacgat tgcccaaatt caagaggcca acattaacca      420
tagaagagca cttttagaaa ggttaacagg ccttggggct gagccatctt taccggaaac      480
ggaggtctca gacagaccct cagattctgc tactccagat gatgcttcta atgcttctca      540
tgctgattaa gaattcgcgg gggatctccc atgtctctac tggtggtggt gcttctttgg      600
tacc                                                                   604

<210> SEQ ID NO 4
<211> LENGTH: 1120
<212> TYPE: DNA
<213> ORGANISM: Synechococcus elongatus
<220> FEATURE:
<221> NAME/KEY: misc_feature
<222> LOCATION: (1)..(64)
<223> OTHER INFORMATION: recombination arms
<220> FEATURE:
<221> NAME/KEY: misc_feature
<222> LOCATION: (65)..(1066)
<223> OTHER INFORMATION: ORF for Prk
<220> FEATURE:
<221> NAME/KEY: misc_feature
<222> LOCATION: (1067)..(1120)
<223> OTHER INFORMATION: recombination arms

<400> SEQUENCE: 4
actagtttac ttcttgctca ttagaaagaa agcatagcaa tctaatctaa gttttaatta       60
caaaatgtct aaaccagata gagttgtttt aatcggtgtt gctggtgatt ctggttgtgg      120
taaatctaca tttcttaaca ggttagctga tttatttggt actgaattaa tgactgttat      180
```

```
ttgtttagat gattatcatt cgttagatcg taaaggcaga aaggaagcgg gtgtaactgc      240
tttagatcct agagctaata attttgattt aatgtatgaa caagttaaag ctttaaaaaa      300
tggtgaaact atcatgaaac caatctataa tcatgaaact ggtttaatcg atccacctga      360
aaagatcgag ccaaacagaa ttattgtaat tgaagggtta cacccacttt atgacgaacg      420
agttcgcgaa cttttagatt tttctgttta tttagatatc gatgatgaag ttaaaatcgc      480
ttggaaaatc caaagagata tggccgaaag aggtcattct tatgaagatg ttttagcctc      540
aattgaggct agaaggccag attttaaagc atatattgaa ccgcaacggg acacgctga      600 tatcgttatt cgtgtaatgc ccactcaact tatcccgaat gacactgaga ggaaagtcct      660
aagggtacaa ttaatccaga gagaaggaag ggatggattt gaaccagctt atttatttga      720
tgaaggttct acaattcaat ggacgccttg tggcagaaag ttaacatgta gctatcctgg      780
cattcgctta gctatggtc cagatactta ttatggtcat gaagtttctg tccttgaagt       840
ggatggacaa tttgaaaatt tagaagaaat gatttacgtt gaaggtcatt tatctaaaac      900
tgatactcaa tattatggtg aattaactca tctactttta caacacaaag attatccagg      960
ttctaataat ggtactggtt tattccaagt gctaacgggt ctcaagatgc gggccgccta     1020
tgaaaggtta acttctcaag ctgctccagt tgctgcttct gtttaagaat tcgcggggga     1080
tctcccatgt ctctactggt ggtggtgctt ctttggtacc                           1120

<210> SEQ ID NO 5
<211> LENGTH: 939
<212> TYPE: DNA
<213> ORGANISM: Rhodobacter sphaeroides

<400> SEQUENCE: 5
cacacactaa attaccggat caattcgggg gatccatgtc taaaaaacat ccaatcatca       60
gtgtaacggg cagttcgggg gcgggaactt caactgtcaa acatactttt gatcaaattt      120
ttcgtcgtga aggcgtcaag gcagtttcta tcgaaggtga tgcttttcat agatttaata      180
gagctgatat gaaagcagag ctcgatcggc gatacgcggc aggtgatgct acttttctc       240 atttttctta tgaagctaat gaactgaaag agctggagag agtgtttcga gaatacgggg      300
aaacggggca gggtcggaca cgtacttatg ttcatgatga tgctgaagcg gcgcggactg      360
gagtcgcgcc aggtaatttt actgattgga gagattttga ttctgattct catttattat      420
tttatgaagg tttacatgga gctgtagtta actctgaggt taacatcgcg ggtctggctg      480
atttaaaaat cggtgttgtt ccagttatca atttagaatg gattcaaaaa atccatagag      540
atagagcgac taggggttat actactgaag cagtcacgga tgtcattcta cgtagaatgc      600
atgcttatgt tcattgtatc gttccacaat tttctcaaac tgatatcaat tttcaacggg      660
tgccggtggt ggatacctct aatccttta ttgctagatg gattcctact gctgatgagt       720
cagtggtagt aattcgtttt cggaatcctc gtggaattga cttccttat cttacatcta       780 tgattcatgg tagttggatg tcgagagcca atagtattgt cgtccctgga aataagctgg      840
acctggccat gcagctcatt ctcacgccgc tgattgacag gctggttcga gaatcaaaag      900
ttgcttaact gcaggagggc cgcatcatgt aattagtta                              939

<210> SEQ ID NO 6
<211> LENGTH: 942
<212> TYPE: DNA
<213> ORGANISM: Rhodopseudomonas palustris
```

```
<400> SEQUENCE: 6
cacacactaa attaccggat caattcgggg gatccatgtc tagaaaacat ccaatcatct      60
ctatcactgg ttcttctggt gctggtacta cttctgttaa aaaaactttt gaacaaatct     120
ttagaagaga aaatgttaat gctgctttta tcgaaggtga tgcttttcat cgatataata     180
gagttgatat gagaaataaa atggctgaag aagctgaaag aggtaataga cattttctc      240 attttctcc agaaactaat ttatttgaag agttagaaca gacttttaga tcttatgctg      300
aaactggtat cggtagaact agacattatg ttcatgatga tgaagaagct gcattacatg     360
gagtcccgcc aggtaatttt actcaatggc aggacctccc tgccaatagt gatttattat     420
tttatgaagg tttacatggt gctgttatca ctgaaaaagt taatgttgct caacatgctg     480
atttaaaaat cggtgttgtt cctgttatca atttagaatg gattcaaaaa ttacatcgcg     540
accgagcggc caggggtac tcgactgagg ctgtcactga tacaatcctt agaagaatgc      600
cagattatgt tcattatatc gttccacaat ttgctgaaac tgatatcaat tttcaaagag     660
ttccaactgt tgatacttct aatccattta tcgctagatg gattccaact gctgatgaat     720
ctatggttgt tatcagattt aaaaatccaa gaggaattga ctttgcgtac ctcttatcta     780
tgatccaagg ttcttttatg tctagagcta attctatcgt tatccatggt gctaaattag     840
atctggcgat gcagcttatt cttactccat taatcatgca gcttatcgat agaaaaagat     900
ctatgaaata actgcaggag ggccgcatca tgtaattagt ta                        942

<210> SEQ ID NO 7
<211> LENGTH: 1275
<212> TYPE: DNA
<213> ORGANISM: Euglena gracilis

<400> SEQUENCE: 7
cacacactaa attaccggat caattcgggg gatccatggc tgtttgtact gtttatacta      60
tccctacaac aactcatctt ggttcatctt ttaatcagaa taataaacag gtcttctttta    120 attataaaag atcatcatca tcaaataaca ccctgttcac aactaggcca tcttatgtta     180
tcacttgttc tcaacaacaa actatcgtta tcggtttagc tgctgattct ggttgtggta     240
aatctacttt tatgagaaga ttaacttctg tttttggtgg tgctgctgaa ccaccaaaag     300
gaggcaaccc tgatagcaat acgttaatct ctgatactac tactgttatt tgtctagatg     360
acttccacag tttagataga aatggtagaa aagttgaaaa agttactgct ttagatccca     420
aggcgaacga ctttgactta atgtatgaac aagttaaagc tttaaaagaa ggtaaagctg     480
ttgataaacc aatttacaac cacgtgtcgg gcctgctcga ccctccggaa ctcattcagc     540
cacccaaaat tctggtcatt gagggattac atcctatgta cgatgctaga gttagagagc     600
tactcgactt ctctatttac ctcgacatct caaatgaagt taaatttgct tggaaaatcc     660
aaagagatat gaaagaaga ggtcattctt tagaatctat caaagcttct atcgaatcta     720
gaaagcctga tttcgatgcg tacatcgatc cacaaaaaca acatgctgat gttgttattg     780
aagtgctccc taccgaactc attccggatg atgatgaagg taaagttttta agagttagaa    840 tgatccaaaa agaaggtgtt aaattttttca acccggtgta ccttttttgat gaaggttcta    900 ctatctcttg gattccatgt ggtagaaaat taacttgttc ttatccaggt atcaagtttt     960
cgtacgggcc agacacattt tacggtaatg aagttactgt tgttgaaatg gatggtatgt    1020
tcgatcgttt agatgagtta atctacgttg agtcacactt atcgaatctg tcaactaaat    1080
tttatggtga agttactcaa caaatgttaa agcatcagaa ttttcctggc agtaataatg    1140
```

```
gaactggttt ttttcaaact atcatcggtc ttaaaattag ggatttattt gaacaattag    1200
ttgcttctag atctactgct actgctactg ctgctaaagc ttaactgcag gagggccgca    1260
tcatgtaatt agtta                                                    1275
```

<210> SEQ ID NO 8
<211> LENGTH: 1434
<212> TYPE: DNA
<213> ORGANISM: Spinacia oleracea

<400> SEQUENCE: 8

```
cacacactaa attaccggat caattcgggg gatccatgag atatgatcaa ctcattcatg      60
agggtccgag acagtcatcg ccttcgcttc tgcaactcgc ttctgttcct gctactgtct     120
tttgtgctgt ttttggtatc ggttatactt tttctggtgg tttagttgaa aattatgcaa     180
ctactcgtcc tgtgcagacg caacccgctg cgttaatcct tccaaaagct gtcaggtatg     240
caggagtatc acaggggccg caggtagagt cacgggaagc cagaacagct ttacatgctg     300
ctgctactgg tactgttaat agagactcaa cgctacaaag gccaaaagtt gatccaaaaa     360
aaactgtttt aatcggggtc gcagctgatt ctggttgtgg taaatctact tttatgagaa     420
gactaactgg tatttttgga ggtggaaaac ccacacctct tggaggtggg tttggtactg     480
gtggttggga aactaatact ttagtttctg ataaaactac tgttatgtgt ttagatgatt     540
atcatttaaa tgatagagct ggtcgtaaag taacgggtct gactgccctt gatcaaagag     600
aaaataattt tgatttaatg tttgaacaaa tgtcttcttt aaaaagagga gaaactatcg     660
ctaaaccaat ctataatcat gttaatggta ctttagatac tccagaagag atcgctccag     720
cttctatcat gatcattgaa ggccttcacc ccctgctaga tgaccgtgtg gctggtttat     780
tagatttttc tatctattta gatatctctg atagagttaa atttgcttgg aaaatccaaa     840
gagatatggc ggagaggggt tgggctttag aagatatcaa aaaagatatc gaaaaaagaa     900
aaccagattt tgataaatat gttgctccac aaagggctaa agctgatatg gtaattgagg     960
tgctccctag taggcttgca cccccaaaag atgaaacggc gccctcgaa tacctccgtg    1020 tgcgattaat ccaaaaaact actactaaac attttgatcc agtttattta atcgaaaaag    1080
gttcttctgt tacttggaaa ccatgtggtg acaacctgca atgcgagtac ccaggattac    1140
agttagctta ttatactgaa gaatatatgg ggcatccggc cgaagtgctc gaaatggacg    1200
gtgttatcca taatttaaaa gaaggtttat atgttgaaaa atttttacat aatactggtg    1260
ctaaagaatt tggagaactc acgcaggaac tccttaaagg tcagaattct ccaggtggtg    1320
ataatggtac tggttttatg caaactttag ctgctttaaa aatcagggaa atttacgaaa    1380
gggctactgg tgaaaaagct taactgcagg agggccgcat catgtaatta gtta          1434
```

<210> SEQ ID NO 9
<211> LENGTH: 1768
<212> TYPE: DNA
<213> ORGANISM: Synechococcus elongatus
<220> FEATURE:
<221> NAME/KEY: misc_feature
<222> LOCATION: (1)..(50)
<223> OTHER INFORMATION: recombination arms
<220> FEATURE:
<221> NAME/KEY: misc_feature
<222> LOCATION: (51)..(1718)
<223> OTHER INFORMATION: ORF for GroEL1
<220> FEATURE:
<221> NAME/KEY: misc_feature
<222> LOCATION: (1719)..(1768)

<223> OTHER INFORMATION: recombination arms

<400> SEQUENCE: 9

```
tttaaaacac caagaactta gtttcgaata aacacacata aacaaacaaa atggctaaat      60
taatcttatt tcatgaagat tcaagacaag cattagaaag gggtgttaat gctttagcta     120
atgctgttaa agttacttta ggtccaagag gtagaaatgt tttattagaa aaaaaatttg     180
gtgctccaga aatcatcaat gatggtgttt ctatcgctaa agaaatcgaa ttagaagatc     240
cacatgaaaa tgcaggtgca agactagttc aagaagttgc tgctaaaact aaagaaatcg     300
ctggtgatgg tactactact gctactgttt tagctcaagc tatcgttaga gaaggtttaa     360
ctaatgttgc tgctggtgct aatccaatcg ttttaagaag aggtatcgaa aaagctgttg     420
ctactttagt tgaagctatc gctgctaaag ctcaaccagt tgctgatgaa gctgctatca     480
gatctatcgc tgctgtttct gctggtaatg atgatgaagt tggtcaaatg atcgctgatg     540
ctgttgctaa agttactaaa gatggtgtta tcacagttga agaatctaaa tctttagcta     600
ctgaattaga agtcgttgaa ggtatgcaat ttgatagagg ttatttatct ccatattttg     660
ttactgatca agatagacaa gtagttgaat atgataatcc attaatctta ttaactgata     720
aaaaaatcgc ttctatccaa gatttagttc cagttttaga agatgttgct agagctggta     780
gaccattatt aatcatcgct gaagatatcg aaggtgaagc tttagctact ttagttgtta     840
ataaagctag aggtgtttta aatactgttg ctgttaaagc tccagctttt ggtgatagaa     900
gaaaagctat cttacaagat atcgctgttt taactggtgg tcaagttatc tctgaagaag     960
ttggtttatc tttagctgat gctaattctt ctgttttagg taaagctcaa aaaatcacta    1020
tctctaaaga tactactatc atcgttgctg gtgatgaaaa taaagctgat gttgctgcta    1080
gaatcgctca aatcagaaga tctttagaag aaactgattc tgattatgat agagaaaaat    1140
tacaagaaag aatcgctaaa ttagctggtg gtgttgctgt tatcaaagtt ggtgctccaa    1200
ctgaaactga attaaaaaat agaaaattaa gaatcgaaga tgctttaaat gctactagag    1260
ctgctatcga agaaggagtt gttccaggtg gtggtactac tttattacat ttagcttctg    1320
cttttaacttc tttacaagct tctttaactg ttgctgatga aaaattaggt gttgaaatcg    1380
ttgctagagc tttagaagct ccattaagac aaattgctga taatgctggt gcagaaggtt    1440
ctgttgttgt cgaaaaatta agagataaag attttaattt tggttataat gctttaactg    1500
gtcaatatga agatttagtt gcttctggta tcttagatcc agctaaagtt gttagatctg    1560
ctttacaaga tgctgcttct gttgcttctt taatcttaac tactgaagtt ttagttgttg    1620
atcaacctga accagaacca gctatgcctg ctggtggtga tatgggtggt atgggtggta    1680
tgggtatgcc tggtatgggt ggtatgggta tgatgtaaga attcacttct aaataagcga    1740
atttcttatg atttatgatt tttattat                                       1768
```

<210> SEQ ID NO 10
<211> LENGTH: 1735
<212> TYPE: DNA
<213> ORGANISM: Synechococcus elongatus
<220> FEATURE:
<221> NAME/KEY: misc_feature
<222> LOCATION: (1)..(50)
<223> OTHER INFORMATION: recombination arms
<220> FEATURE:
<221> NAME/KEY: misc_feature
<222> LOCATION: (51)..(1685)
<223> OTHER INFORMATION: ORF for GroEL2
<220> FEATURE:
<221> NAME/KEY: misc_feature
<222> LOCATION: (1686)..(1735)
<223> OTHER INFORMATION: recombination arms

<400> SEQUENCE: 10

```
tttaaaacac caagaactta gtttcgaata acacacata aacaaacaaa atggctaaaa      60
gaatcatcta taatgaaaat gctagaagag ctttagaaaa aggtatcgat atcttagctg    120
aagctgttgc tgttactttta ggtccaaaag gtagaaatgt cgtcttagaa aagaaatttg   180
gtgcaccaca aattatcaat gatggtgtta ctatcgctaa agaaatcgaa ttagaagatc   240
atatcgaaaa tactggtgtt gctttaatca gacaagcagc ttcaaaaaca aatgatgctg   300
ctggtgatgg tactactact gctactgttt tagctcatgc tgttgtcaaa gaaggtttaa   360
gaaatgttgc tgctggtgct aatgctatct tattaaaaag aggtatcgat aaagctacaa   420
attttcttgt cgaacaaatt aaatcacatg ctcgtccagt cgaagattct aaatctatcg   480
cacaagttgg tgcaatctct gctggtaatg attttgaagt tggtcaaatg atcgctgatg   540
ctatggataa agttggtaaa gaaggtgtta tctctttaga agaaggtaaa tctatgacta   600
ctgaattaga agttactgaa ggtatgcgtt ttgataaagg ttatatctct ccatattttg   660
ctactgatac tgaaagaatg gaagccgtct ttgatgaacc atttatctta atcactgata   720
aaaaaatcgg attagttcaa gatcttgtcc cagttttaga acaagttgct agagctggta   780
gaccattagt tattatcgca gaagatatcg aaaagaagc tttagctact ttagttgtta   840
atagattaag aggtgtctta aatgttgcag ctgtcaaagc tccaggtttt ggtgatagaa   900
gaaaagctat gttagaagat atcgctgttc ttacaggtgg tcaacttatc acagaagatg   960
ctggtttaaa attagatact actaaattag atcaattagg taaagctaga agaatcacta  1020
tcactaaaga taatactact atcgttgctg aaggtaatga agctgctgtt aaagctagag  1080
tcgatcaaat tagaaggcaa attgaagaaa cagaaagctc ttatgataaa gaaaagttac  1140
aagaaagatt agctaaatta tctggtggtg tcgcagttgt caaagttggt gctgctactg  1200
aaactgaaat gaaagataga aaattaagat tagaagatgc tatcaatgct actaaagctg  1260
ctgttgaaga aggtatcgtt ccaggtggtg gtactacttt agctcattta gctccacaat  1320
tagaagaatg ggcaactgct aatttatctg gtgaagaatt aactggtgct caaatcgttg  1380
ctagagcttt aactgctcca ttaaaaagaa tcgctgaaaa tgctggttta aatggtgctg  1440
ttatctctga aagagtcaaa gaattaccat ttgatgaagg ttatgatgca tcaaataatc  1500
aatttgttaa tatgtttact gctggtattg ttgatccagc taaagttaca agatcagctt  1560
tacaaaatgc tgcttctatc gctgctatgg ttttaactac tgaatgtatc gttgttgata  1620
aaccagaacc aaaagaaaaa gctccagctg gtgctggtgg tggtatgggt gattttgatt  1680
attaagaatt cacttctaaa taagcgaatt tcttatgatt tatgattttt attat        1735
```

<210> SEQ ID NO 11
<211> LENGTH: 412
<212> TYPE: DNA
<213> ORGANISM: Synechococcus elongatus
<220> FEATURE:
<221> NAME/KEY: misc_feature
<222> LOCATION: (1)..(50)
<223> OTHER INFORMATION: recombination arms
<220> FEATURE:
<221> NAME/KEY: misc_feature
<222> LOCATION: (51)..(362)
<223> OTHER INFORMATION: ORF for GroES
<220> FEATURE:
<221> NAME/KEY: misc_feature
<222> LOCATION: (363)..(412)

```
<223> OTHER INFORMATION: recombination arms

<400> SEQUENCE: 11
attcctctag tcttgcaaaa tcgatttaga atcaagatac cagcctaaaa atggctgccg        60
tctcattatc tgtttctact gttactccat taggtgatag agtttttgtt aaagttgctg       120
aagctgaaga aaaaactgct ggtggtatca tcttaccaga taatgctaaa gaaaaaccac       180
aagtcggtga aattgtcgct gttggtccag gtaaaagaaa tgatgatggt tcaagacaag       240
ctccagaagt taaaatcggt gataaagttt tatattctaa atatgctggt actgatatta       300
aattaggtaa tgatgattat gttcttttat ctgaaaaaga tatcttagct gttgtcgctt       360
aagaattcat catgtaatta gttatgtcac gcttacattc acgccctccc cc              412
```

YEASTS MODIFIED TO USE CARBON DIOXIDE

CROSS REFERENCE TO RELATED APPLICATIONS

This application is the National Stage of International Application No. PCT/IB2015/050346, filed on Jan. 16, 2015, which claims the benefit of French Provisional Application No. 14 50349, filed on Jan. 16, 2014. The contents of both applications are hereby incorporated by reference in their entirety.

The invention relates to the creation of modified yeast strains with the aim of enabling them to use carbon dioxide as a carbon source.

Human and industrial activity generates increasing amounts of carbon dioxide, which is a main factor of the greenhouse effect, responsible for global warming of the planet likely to cause major climate change.

Carbon dioxide capture and transformation into organic compounds are naturally carried out by certain organisms, in particular in the context of photosynthesis.

Photosynthesis comprises two phases: during the first phase photochemical reactions intervene, at the conclusion of which light energy is converted into chemical energy in the form of ATP and NADPH/NADH; during the second phase, called the Calvin cycle, this chemical energy is used to incorporate carbon coming from carbon dioxide in organic molecules.

The key enzyme of the Calvin cycle is the ribulose-1,5-bisphosphate carboxylase/oxygenase (RuBisCO) complex which converts ribulose-1,5-diphosphate into two molecules of 3-phosphoglycerate by capturing a carbon dioxide molecule.

Several forms of RuBisCO exist (Tabita et al., J Exp Bot, 59, 1515-24, 2008), of which the most represented are form I and form II. Form I consists of two types of subunits: large subunits (RbcL) and small subunits (RbcS). The functional enzyme complex is a hexadecamer made up of eight L subunits and eight S subunits. Correct assembly of these subunits further requires the intervention of at least one specific chaperone: RbcX (Liu et al., Nature, 463, 197-202, 2010). Form II is much simpler: it is a dimer formed of two identical RbcL subunits.

Ribulose-1,5-diphosphate, the substrate of RuBisCO, is formed by reaction of ribulose-5-phosphate with ATP; this reaction is catalyzed by a phosphoribulokinase (PRK). Two classes of PRKs are known: class I enzymes, encountered in proteobacteria, are octamers, whereas those of class II, found in cyanobacteria and plants, are tetramers or dimers.

Non-photosynthetic organisms, such as yeasts, possess neither RuBisCO nor phosphoribulokinase, but contain on the other hand the other Calvin cycle enzymes, because they also intervene in general metabolism of pentoses.

It has been proposed to introduce RuBisCO and PRK into yeasts in order to recreate a Calvin cycle and to enable them to use carbon dioxide. For example, Guadalupe-Medina et al. (Biotechnology for Biofuels, 6, 125, 2013) report that expression in *Saccharomyces cerevisiae* of the form II RuBisCO enzyme from *Thiobacillus denitrificans* and of the PRK from *Spinacia oleracea* improves ethanol production by decreasing glycerol formation.

However, up to now, it had not been possible to express in yeast a bacterial form I RuBisCO enzyme. Indeed, because of the complexity of this form, reconstitution of a functional enzyme requires co-expression in a suitable stoichiometry of the RbcL and RbcS subunits as well as the chaperone RbcX, and the correct association of these subunits in the enzyme complex. However, transposition to a eukaryotic organism of expression stoichiometry, which in prokaryotes is provided by the organization of genes into operons, poses problems. Moreover, existing differences between eukaryotes and prokaryotes in terms of intracellular environment can be reflected in particular in post-translational modifications interfering with folding of peptide chains constituting the enzyme subunits and/or with assembly of these subunits.

The Inventors however succeeded in expressing in yeast the various subunits of the form I RuBisCO enzyme from *Synechococcus elongatus* and in obtaining the assembly of these subunits in order to reconstitute the enzyme complex, by co-expressing these subunits with the specific chaperone RbcX, and with the general bacterial chaperones GroES and GroEL.

The present invention thus has as an object a transformed yeast cell, preferably a *Saccharomyces cerevisiae* cell, characterized in that it contains:

a) an expression cassette containing a sequence encoding the RbcL subunit of a bacterial form I RuBisCO enzyme, under the transcriptional control of a suitable promoter;

b) an expression cassette containing a sequence encoding the RbcS subunit of said RuBisCO enzyme, under the transcriptional control of a suitable promoter;

c) an expression cassette containing a sequence encoding the specific chaperone RbcX of said RuBisCO enzyme, under the transcriptional control of a suitable promoter;

d) an expression cassette containing a sequence encoding a bacterial chaperone GroES, under the transcriptional control of a suitable promoter;

e) an expression cassette containing a sequence encoding a bacterial chaperone GroEL, under the transcriptional control of a suitable promoter.

A particularly novel character of the invention is that the chaperones mentioned in points c), d) and e) above preferably belong to two different organisms. Preferably, the three chaperones belong to at least two distant Gram-negative bacterial species, of which at least one is a cyanobacterium. For example, the general chaperones (GroES, GroEL) come from *E. coli* and the "specific" chaperone (RbcX) comes from *Synechococcus elongatus*. The sequence similarity of the chaperones (% of identical amino acids in alignment) is 61% between GroEL1 from *S. elongatus* and GroEL from *E. coli*; 56% between GroEL2 from *S. elongatus* and GroEL from *E. coli*; 63% between GroEL1 and GroEL2 from *S. elongatus*. A threshold of 65% identity thus distinguishes the general chaperones from *E. coli* and *S. elongatus*. In the present text, "GroES" and "GroEL" designate any protein having chaperone activity and having between 65% and 100% amino acid identity with GroES and GroEL from *E. coli* K 12, respectively. The chaperone activity of a variant of the general chaperones GroES and GroEL from *E. coli* could be verified for example by substituting, in the various examples of implementation of the invention described, the expression cassette encoding native GroES or GroEL from *E. coli* by variants of chaperones to be evaluated.

The chaperone RbcX is very distant from GroEL and GroES and its sequence cannot be aligned with the sequences of these two chaperones. In the present text, "RbcX" designates any cyanobacterium chaperone having more than 50% sequence identity (in amino acids) with the chaperone RbcX encoded by SEQ ID NO: 3 and retaining the specific chaperone activity of this protein (which can be verified in a yeast expressing the RbcL and RbcS subunits of RuBisCO from *S. elongatus*, by replacing the expression cassette including SEQ ID NO: 3 of the invention by any other sequence to be evaluated, and by measuring by an in vitro test on cellular extracts the RuBisCO activity thus obtained). Preferably, the present invention is implemented with a chaperone RbcX whose sequence identity (in amino acids) to the chaperone RbcX encoded by SEQ ID NO: 3 is higher than 80%, indeed higher than 90%.

According to a preferred implementation of the present invention, the chaperone RbcX is a cyanobacterial chaperone, for example from *Synechococcus elongatus*.

According to another preferred implementation of the present invention, at least one of the general chaperones GroES and GroEL comes neither from a cyanobacterium nor from another bacterium expressing a RuBisCO complex.

According to an advantageous embodiment, the three expression cassettes form a continuous block of genetic information. It can also be advantageous that the expression cassettes of the three chaperones are carried by a single episomal genetic element.

Preferably, the bacterial form I RuBisCO enzyme is a cyanobacterial RuBisCO enzyme, advantageously from a cyanobacterium of the genus *Synechococcus* and most preferably from *Synechococcus elongatus*.

According to a preferred embodiment of the present invention, the aforesaid cell further contains an expression cassette f) containing a sequence encoding a PRK, preferably a class II PRK, for example a PRK from *Spinacia oleracea*, *Euglena gracilis* or *Synechococcus elongatus*, under the transcriptional control of a suitable promoter.

A wide variety of tools (promoters, expression vector cassettes, transformation methods) usable for expressing genes of interest in yeast cells is available in the art (for a review see for example "Methods in Yeast Genetics" D. Amberg, D. Burke and J. Strathem, Cold Spring Harbor Laboratory Press, 2005).

Promoters usable in the context of the present invention include constitutive promoters, namely promoters which are active in most cellular states and environmental conditions, as well as inducible promoters which are activated or repressed by exogenous physical or chemical stimuli, and which thus induce a variable level of expression as a function of the presence or absence of these stimuli.

For the expression cassettes a) to e), constitutive promoters such as, for example, TEF1, TDH3, PGI1, PGK, ADH1 will preferably be used. Preferably, these promoters will be different from one cassette to another.

For the PRK expression cassette f), an inducible promoter will preferably be used. For example, mention may be made of the tetO-7 promoter, whose expression is repressed by doxycycline and thus induced by the absence thereof.

Other inducible promoters usable in the context of the present invention are in particular the tetO-2, GAL10, GAL10-cyc1, PHO5 promoters.

The expression cassettes of the invention further comprise sequences common to this type of construction, such as transcription terminators, and if need be other transcription regulatory elements such as amplifiers.

The relative stoichiometry of proteins expressed by the various expression cassettes is likely to play an important role in the optimal implementation of the present invention. The system of co-expression in yeast described in the experimental part below is particularly relevant in this respect. The invention however is not limited to the use of this system, and it can be implemented with any variant of expression of the elements mentioned having effects at least equivalent, such that they can be measured, for example, by reproducing one of the examples described below.

The expression cassettes according to the invention can be inserted into chromosomal DNA of the host cell, and/or carried by one or more extrachromosomal replicon(s).

The yeast strains according to the invention can be grown under common culture conditions for strains of the same species. Advantageously, these cultures will be prepared under an atmosphere containing at least 90% carbon dioxide.

The present invention will be better understood with the help of the further description that follows, which refers to non-limiting examples describing expression of a RuBisCO complex and a PRK in *Saccharomyces cerevisiae*.

FIGURE LEGENDS

FIG. 1: Analysis of total lysates of transformed strains. 1A: SDS-PAGE analysis of total lysate of strains 11.5, 11.15, 11.7, 11.17, 11.9, 11.19, 11.5, 11.19; 1B: analysis by anti-HA immunodetection of total lysate of strains 14.5, 14.12, 14.6, 14.7, 16.3, 16.5, 16.6.

Figure 2:
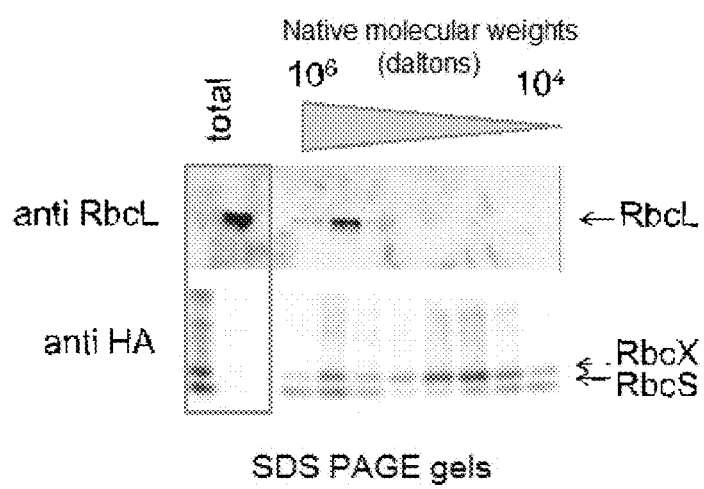

FIG. 2: Analysis by immunodetection of total lysate (box on the left of the Figure), and of fractions sorted by molecular weight, of strain 16.5, which co-expresses RbcL, RbcS, and RbcX, and of its control, strain 16.3, which expresses RbcX.

Figure 3:
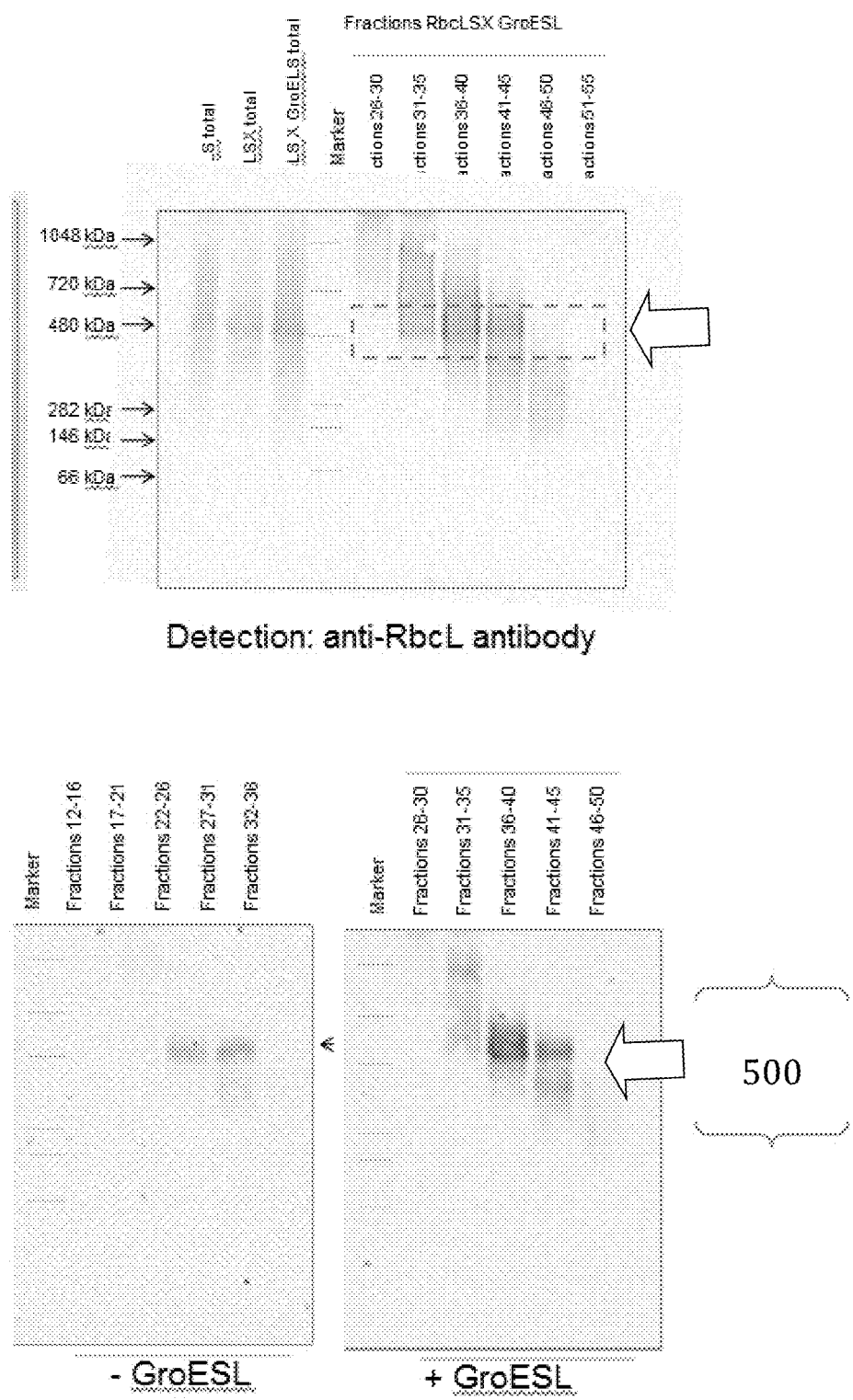

FIG. 3: Analysis on nondenaturing gel, followed by immunodetection using an anti-RbcL antibody, of total extracts of strains 11.9, 18.3 and 22.2, and of fractions sorted by molecular weight of strain 22.2, which co-expresses RbcL, RbcS, and RbcX from *S. elongatus* and chaperones from *E. coli*. Then, in parallel, the fractions sorted by molecular weight of strains 18.3 (on the left) and 22.2 (on the right).

Figure 4:
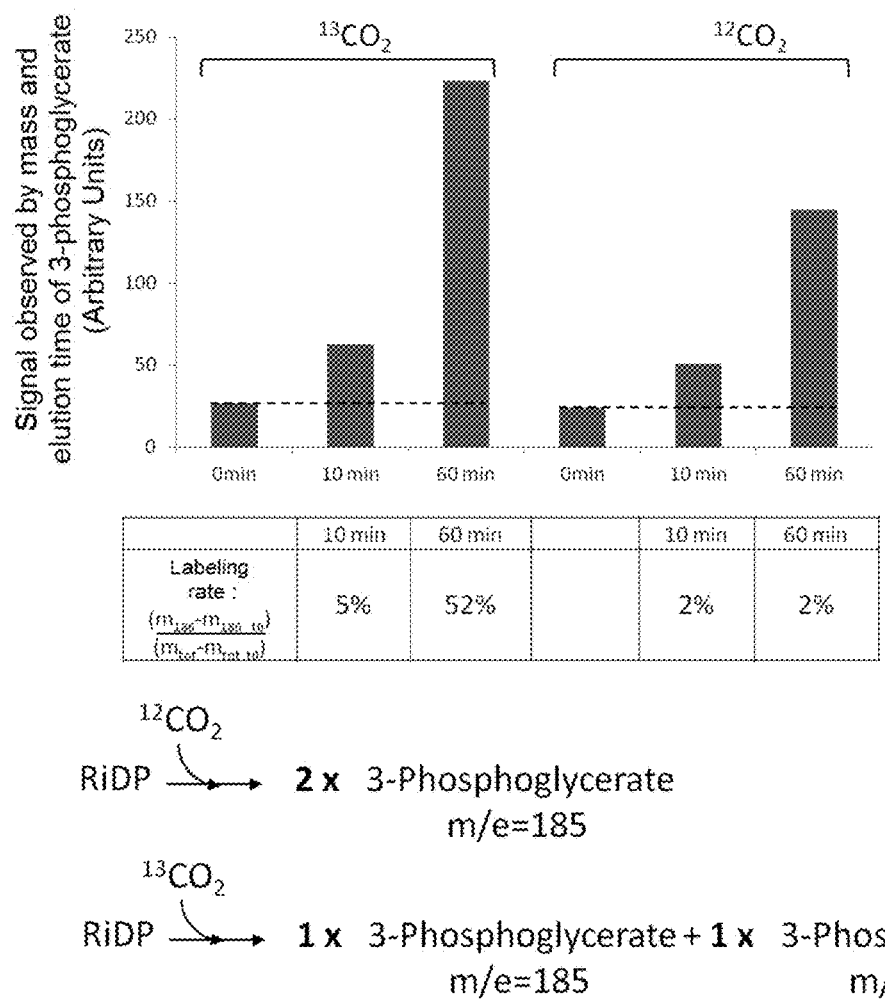

FIG. 4: Amount of 3-phosphoglycerate detected (m/e of 185 and 186, i.e. ions of unlabeled 3-phosphoglycerate and $^{13}C$-labeled 3-phosphoglycerate on a carbon in ES$^-$) obtained at various reaction times (0.10 and 60 minutes). On the left are shown the experiments carried out in the presence of $^{13}CO_2$ and on the right those carried out in the presence of $^{12}CO_2$.

Figure 5:
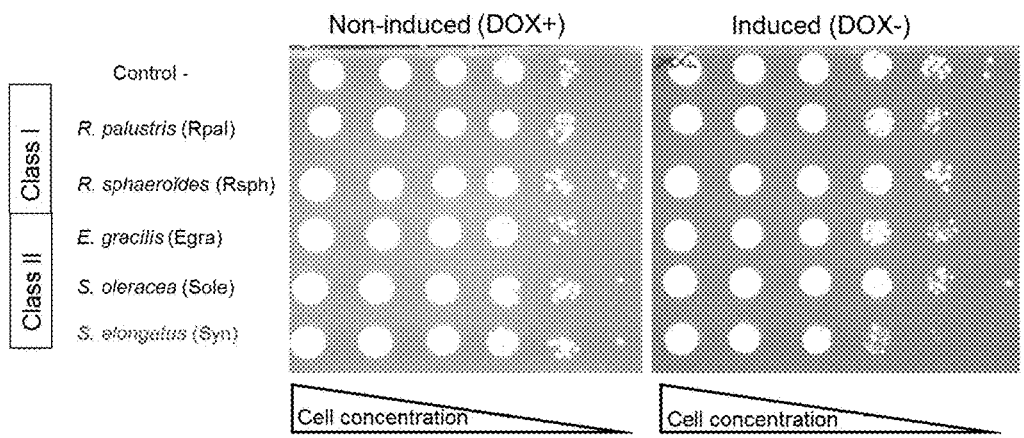
Figure 5:
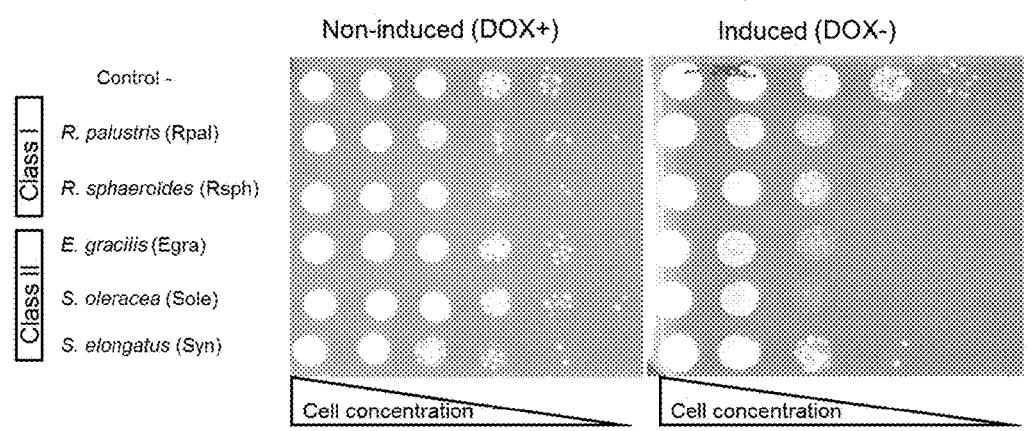

FIG. 5: Influence of the expression of various PRKs on cell viability, in normal atmosphere. Each strain is grown in liquid on selective CSM medium with 2 µg/ml doxycycline. An equivalent of 2 OD (OD at 600 nm) is collected then washed twice to remove the doxycycline. Tenfold dilutions are prepared. 10 µl of the dilutions is deposited in the form of drops (series of serial dilutions) of the cell suspensions, on agar plates (containing or not containing 2 µg/ml doxycycline) and incubated at 28° C. in normal atmosphere.

Figure 6:
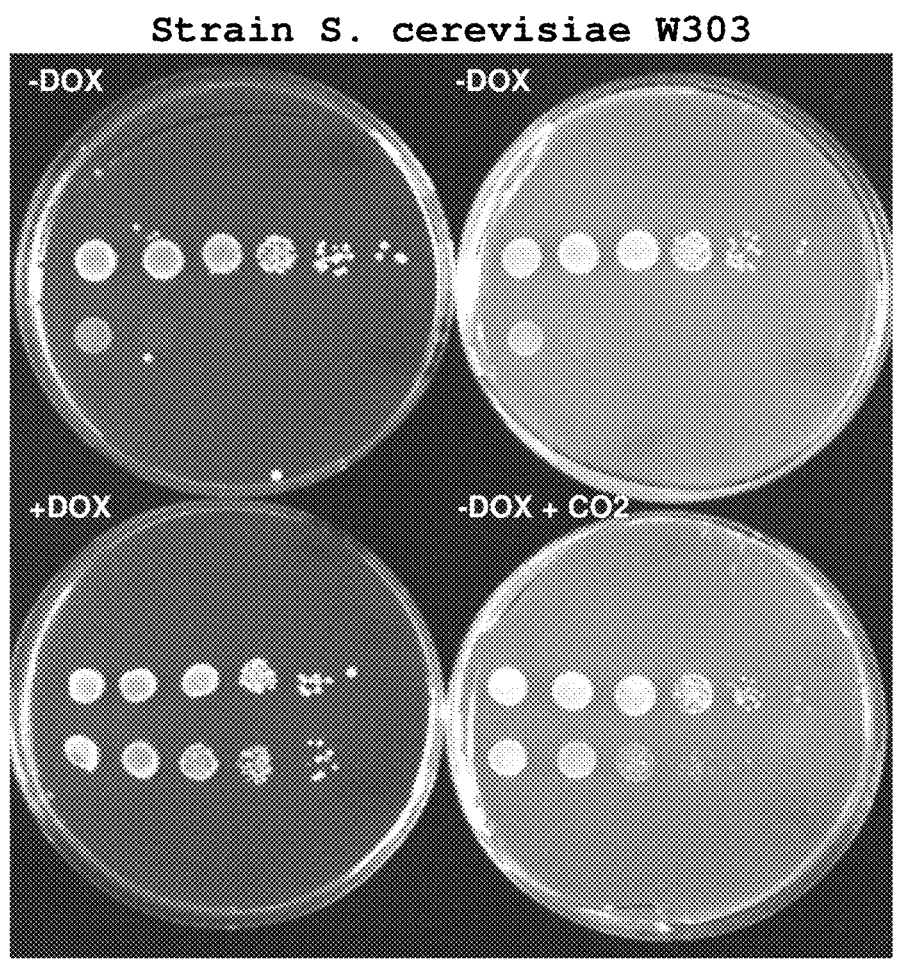

FIG. 6: Influence of the expression of various PRKs on cell viability, in $CO_2$-rich atmosphere. Each strain is grown in liquid on selective CSM medium with 2 µg/ml doxycycline. An equivalent of 2 OD (OD at 600 nm) is collected then washed twice to remove the doxycycline. Tenfold dilutions are prepared. 10 µl of the dilutions is deposited in the form of drops (series of serial dilutions) of the cell suspensions, on agar plates (containing or not containing 2 µg/ml doxycycline) and incubated at 28° C. in closed bags the atmosphere of which contains at least 90:10 (v/v) carbon dioxide/air.

Figure 7:
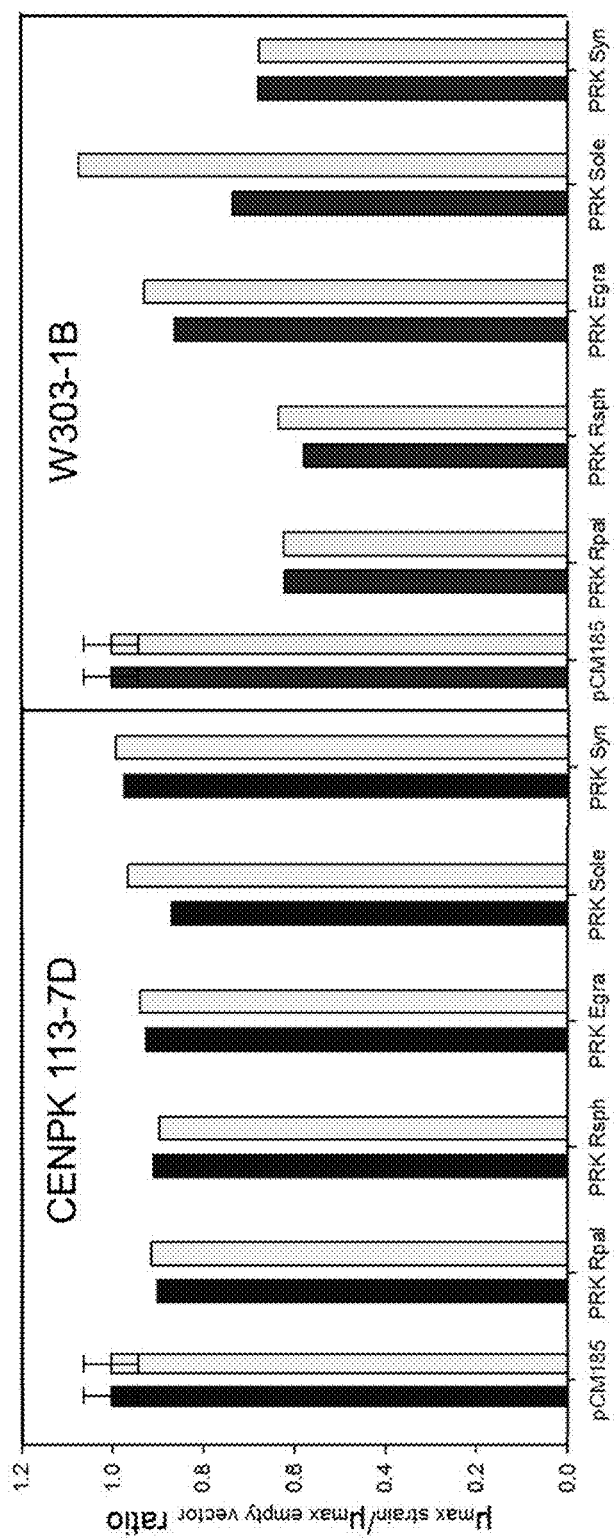

FIG. 7: Maximum growth rate µ ($µ_{max}$) ratios for each strain. Dark bars: induced state (high level of expression) of the tetO promoter (medium not containing doxycycline); light bars: (partially) repressed state (low level of expression) of the tetO promoter (medium containing 2 µg/ml doxycycline).

Figure 8:
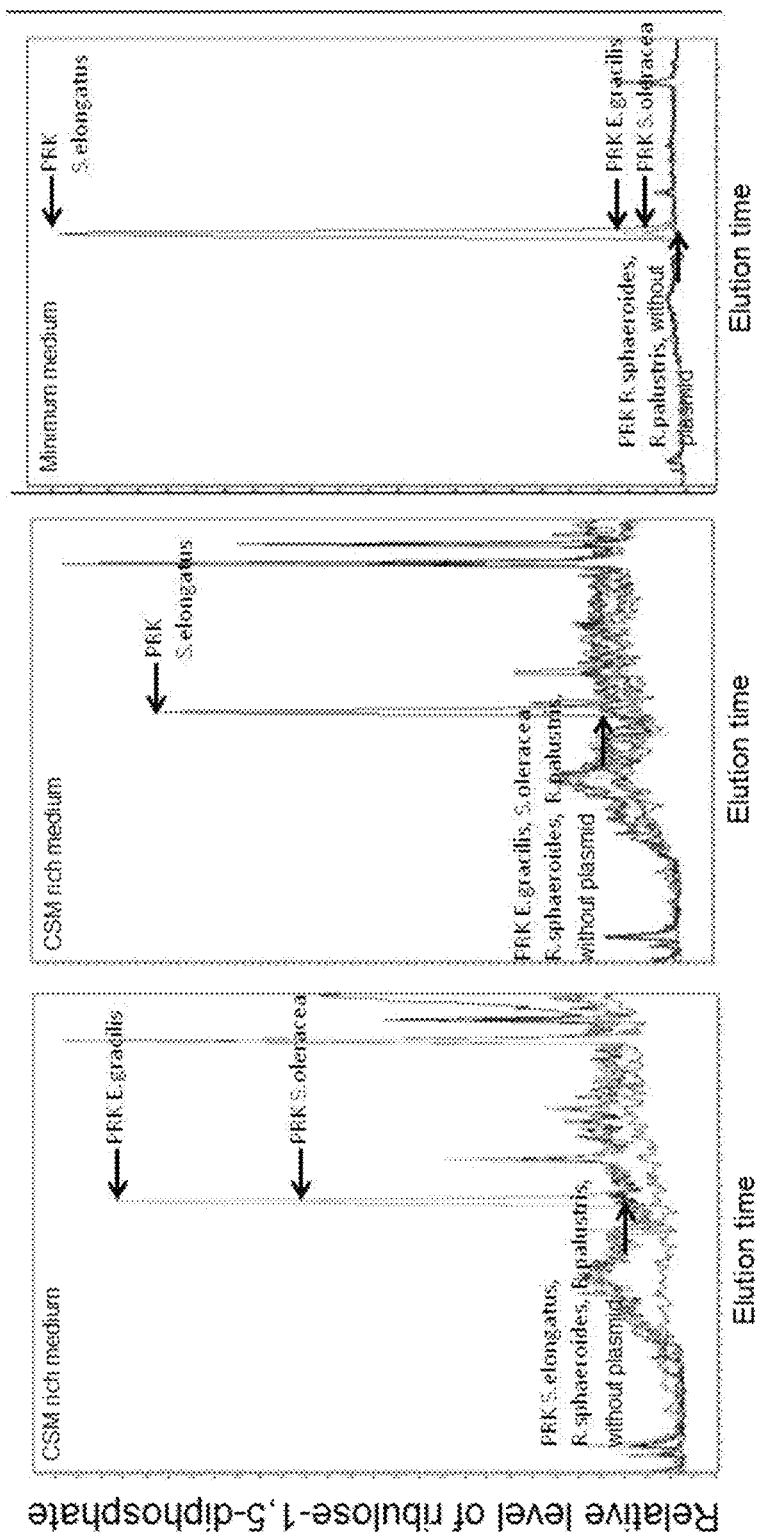

FIG. 8: Detection of ribulose-1,5-diphosphate (molar mass 309 g/mol) as a function of elution time in various extracts. The panel on the left shows the chromatograms of strain W303-1B grown in closed tubes containing selective CSM medium; the panel at center shows the chromatograms of strain CENPK grown in closed tubes and selective CSM medium, the panel on the right represents the chromatograms obtained for strain CENPK grown in closed tubes and minimum medium.

Figure 9:
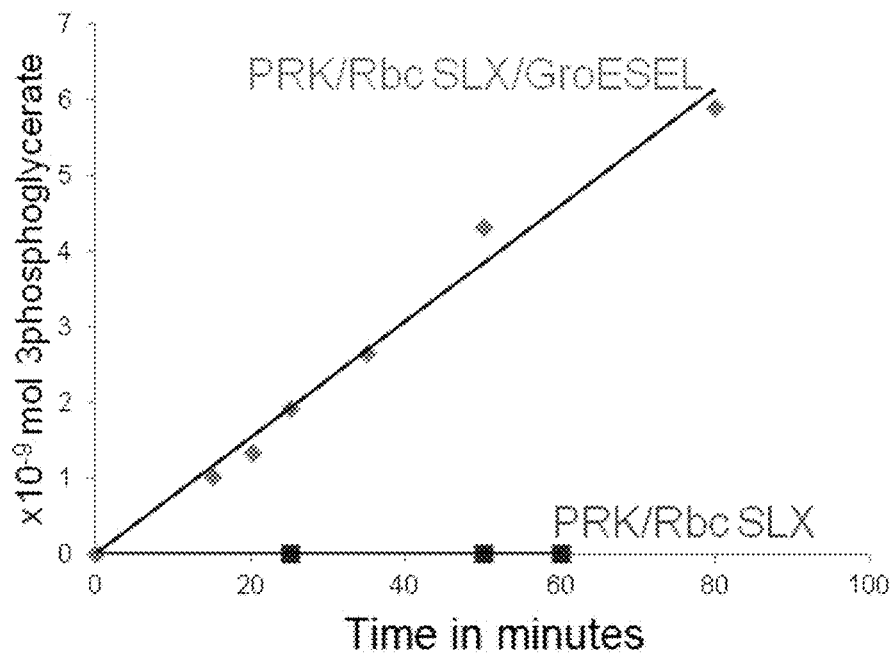

FIG. 9: Evaluation of enzyme activity of synthetic RuBisCO complex on strains CEN.PK no. 3 and 4. PRK: phosphoribulokinase; RbcSLX: products of RbcL, RbcS and RBCX genes; GroESL: products of GroEL and GroEL genes from E. coli.

Figure 10:
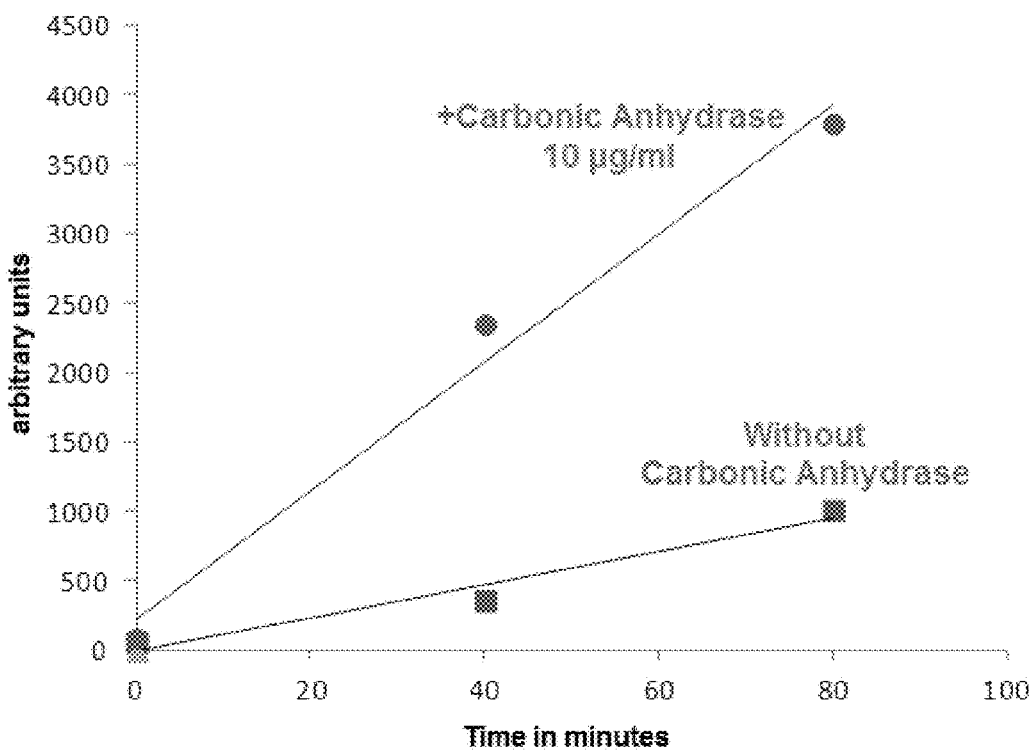

FIG. 10: RuBisCO activity of an extract of yeast CEN-PK no. 3 containing the complete engineering, in the presence and the absence of bovine carbonic anhydrase.

Figure 11:
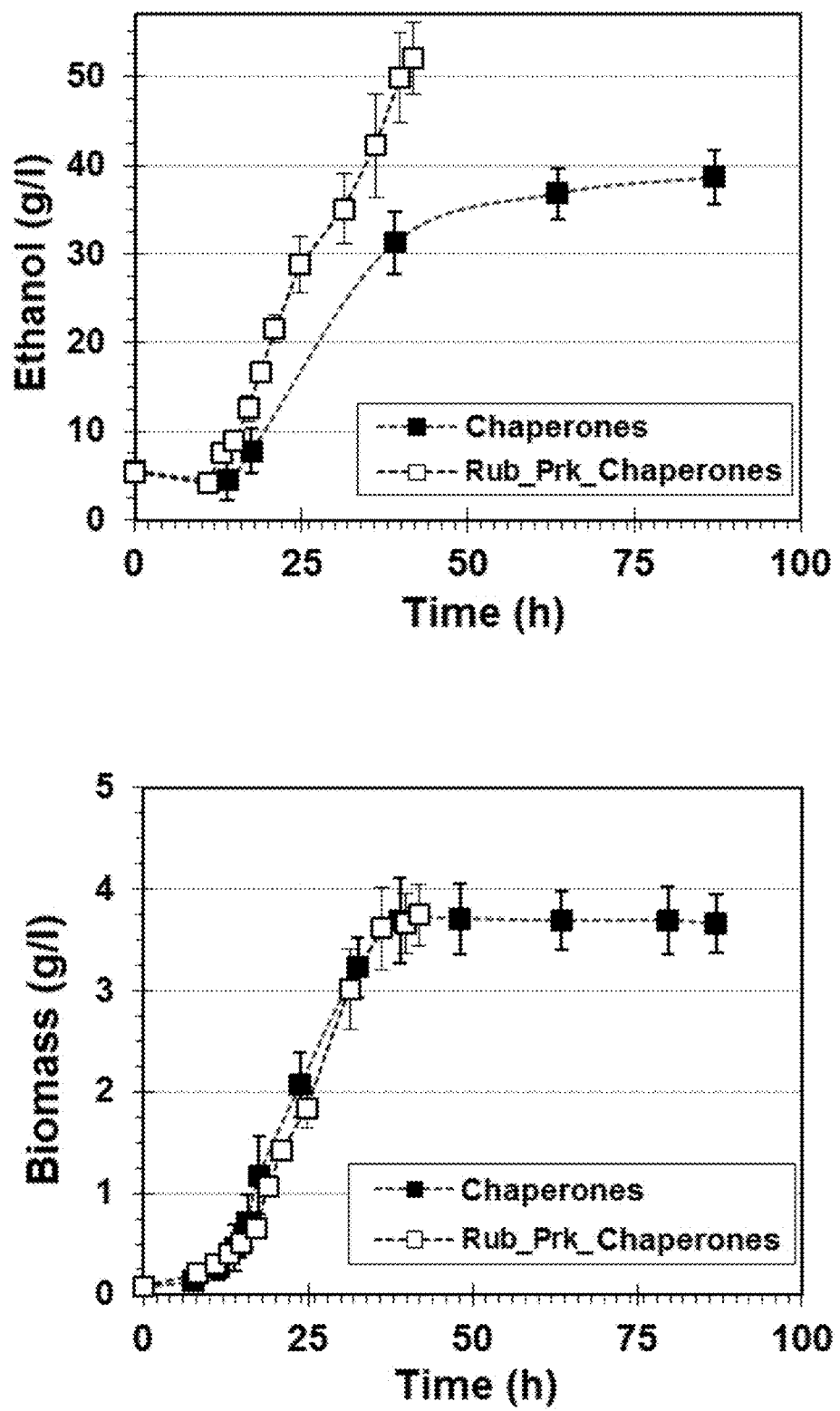

FIG. 11: Change in ethanol and biomass concentration during anaerobic cultures (Rub: RbcS+RbcL; Prk: phosphoribulokinase; Chaperones: RbcX+(GroES+GroEL) E. coli). ■ strain CEN.PK no. 13b and □ strain CEN.PK no. 3.

Figure 12:
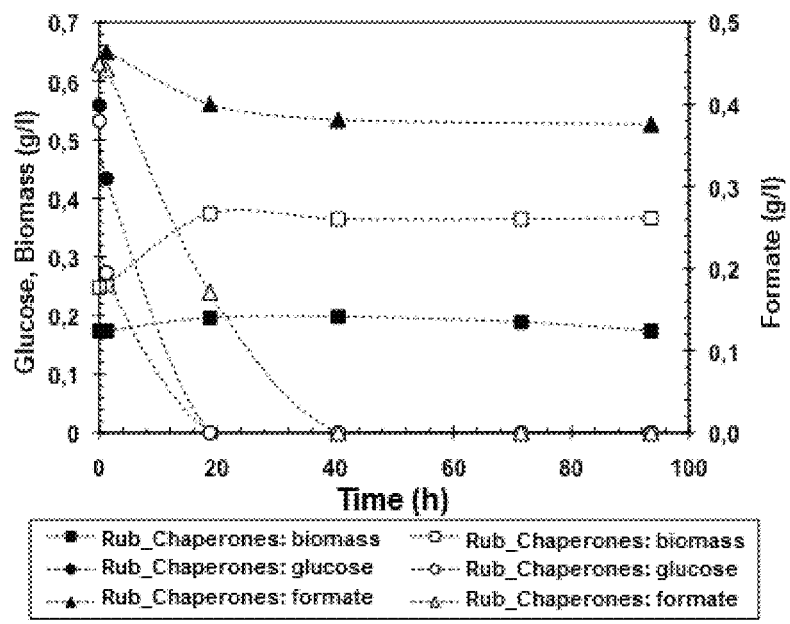

FIG. 12: Change in concentrations of biomass, formate and glucose during aerobic cultures (Rub: RbcS+RbcL; Prk: phosphoribulokinase; Chaperones: RbcX+(GroES+GroEL) E. coli). Biomass generation (g/l, left-hand ordinate): ■ strain CEN.PK no. 2 (RbcL, RbcS, RbcX, GroES_coli, GroEL_coli), □ strain CEN.PK no. 3 (PRK, RbcL, RbcS, RbcX, GroES_coli, GroEL_coli); Glucose consumption (g/l, left-hand ordinate): ● strain CEN.PK no. 2, ○ strain CEN.PK no. 3; Formate consumption (g/l, right-hand ordinate): ▲ strain CEN.PK no. 2, △ strain CEN.PK no. 3.

Figure 13:
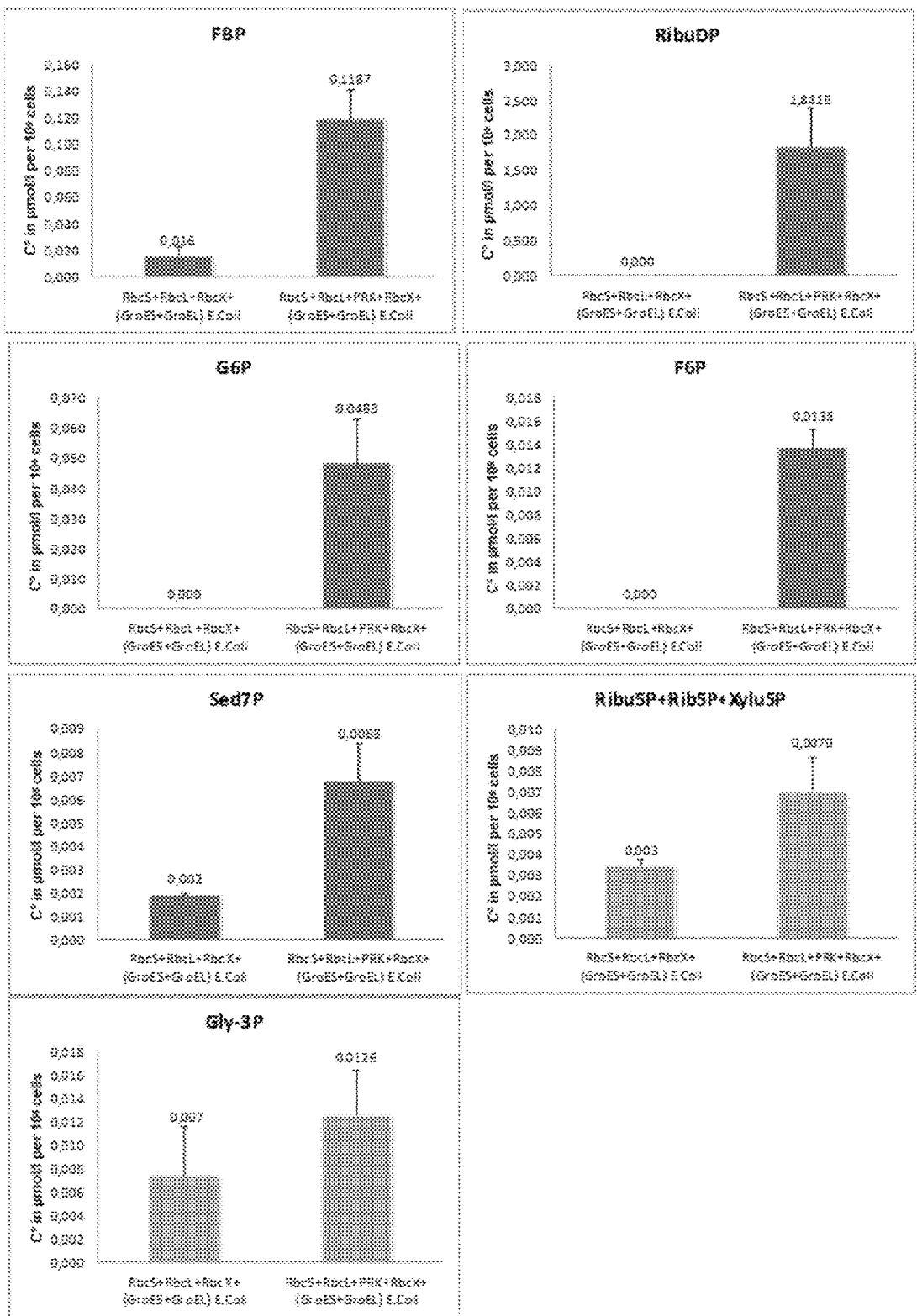

FIG. 13: Extracts of metabolomic analysis carried out strains comprising the complete engineering (CEN.PK no. 3 (PRK, RbcL, RbcS, RbcX, GroES_coli, GroEL coli)) or without PRK (CEN.PK no. 2 (RbcL, RbcS, RbcX, GroES_coli, GroEL_coli)). The analysis shows in particular a strong accumulation of Fructose-6P (F6P), Fructose-1, 6diP (FBP), Glucose-6P (G6P), Sedoheptulose-7P (S7P), Xylolose-5P (Xylu5P), Ribulose-5P (Ribu5P), Ribose-5P (Rib5P), Ribulose-1,5diP (RibuDP) and Glycerate-3P (Gly3P).

Figure 14:
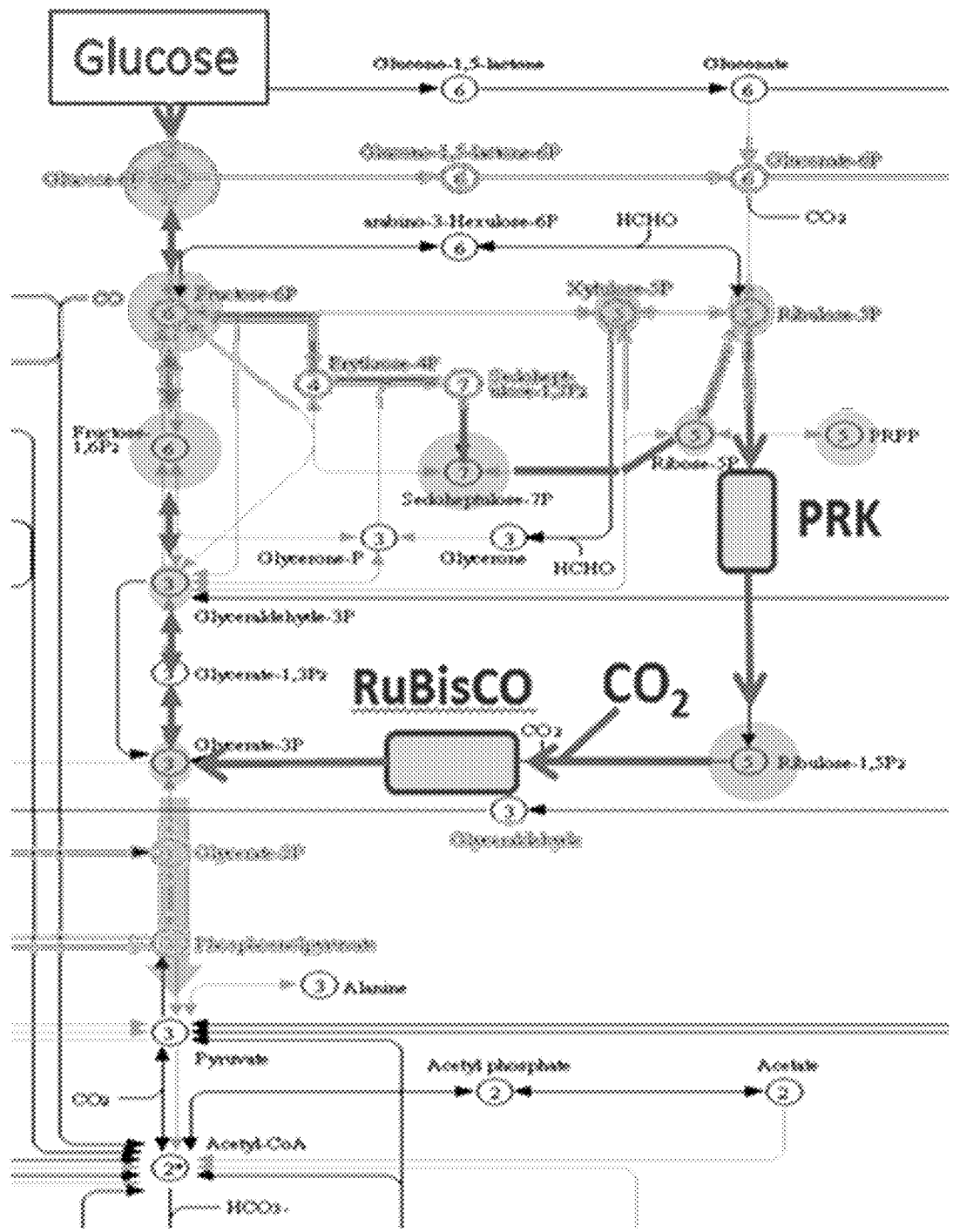

FIG. 14: Metabolic simulation for a modified yeast cell according to the invention.

EXAMPLE 1: Expression and Assembly of the Synechococcus elongatus Rubisco Complex in the Yeast Saccharomyces cerevisiae Synthetic genes encoding the RbcS and RbcL subunits and the specific chaperone RbcX of the RuBisCO from Synechococcus elongates pCC6301, and optimized for expression in yeast, were prepared and cloned into the plasmid pBSII (Genecust). Variants in which an HA tag was added at the 3' end of the coding sequence were also constructed.

The sequences of these synthetic genes (with no HA tag) are indicated in the appended sequence list under numbers SEQ ID NO: 1 (RbcL), SEQ ID NO: 2 (RbcS) and SEQ ID NO: 3 (RbcX).

The sequences encoding the E. coli chaperones GroES and GroEL were amplified from E. coli cultures and cloned into the plasmid pSC-B-amp/kan (Stratagene).

The sequences collected from the cloning vectors were introduced into yeast expression vectors. These host vectors are listed in Table I below.

TABLE I

| Names | Yeast origin of replication | Selection marker | Transcription cassette (promoter-terminator) | E. coli replicon |
|---|---|---|---|---|
| pFPP5 | 2u | URA3 | pGAL10-CYC1-tPGK | Yes (AmpR) |
| pFPP10 | 2u | URA3 | pTDH3- -tADH | Yes (AmpR) |
| pFPP11 | 2u | URA3 | pTDH3- -tCYC1 | Yes (AmpR) |
| pFPP12 | 2u | URA3 | pTGI1- -tCYC1 | Yes (AmpR) |
| pFPP13 | ARS-CEN6 | LEU2 | pTEF1-tPGK | Yes (AmpR) |

Note:
pGAL10-CYC1: synthetic promoter composed of the UAS of the GAL10 gene and the transcription initiation of the CYC1 gene (Pompom et al., Methods Enzymol, 272, 51-64, 1996).

The expression cassettes thus obtained are listed in Table II below.

TABLE II

| Names | Promoter | Open reading frame | Tag | Terminator |
|---|---|---|---|---|
| CAS1 | TEF1p | RbcL- | HA | PGK |
| CAS2 | TEF1p | RbcS- | HA | PGK |
| CAS3 | TEF1p | RbcX- | HA | PGK |
| CAS4 | PGI1p | RbcX | None | CYC1 |
| CAS5 | TDH3p | RbcL- | HA | ADH1 |
| CAS6 | TDH3p | RbcL | None | ADH1 |
| CAS16 | TEF1 | RbcS | None | PGK |
| CAS17 | TDH3 | RbcL- | HA | PGK |
| CAS18 | TDH3 | RbcL | None | ADH |
| CAS19 | TEF1p | RbcX | None | PGK |
| CAS20 | PGI1 | RbcX- | HA | CYC1 |
| CAS21 | PGI1p | GroES | None | CYC1 |
| CAS22 | TDH3 | GroEL | None | ADH |

In certain vectors, two or three cassettes were inserted. To that end, the plasmids were amplified in the bacterium Escherichia coli DH5α and prepared by maxiprep, then digested by suitable restriction enzymes. Lastly, the fragments are integrated into host vectors by ligation by T4 ligase (Fermentas). The list of vectors constructed is indicated in Table III below.

TABLE III

| Names | Origin type | Cassette 1 | Cassette 2 | Cassette 3 | Markers | Host vector |
|---|---|---|---|---|---|---|
| pFPP6 | 2u | CAS1 | None | None | URA3 | pFPP5 |
| pFPP7 | 2u | CAS2 | None | None | URA3 | pFPP5 |
| pFPP18 | 2u | CAS2* | CAS6 | None | URA3 | pFPP5/pFPP10 |
| pFPP19 | 2u | CAS2 | CAS6 | None | URA3 | pFPP5/pFPP10 |
| pFPP23 | ARS416-CEN6 | CAS3 | None | None | LEU2 | pFPP13 |
| pFPP40 | 2u | CAS5 | None | None | URA3 | pFPP10 |
| pFPP45 | 2u | CAS6 | CAS16 | None | URA3 | pFPP5/pFPP10 |
| pFPP48 | 2u | CAS20 | None | None | URA3 | pFPP12 |

TABLE III-continued

| Names | Origin type | Cassette 1 | Cassette 2 | Cassette 3 | Markers | Host vector |
|---|---|---|---|---|---|---|
| pFPP49 | 2u | CAS19 | None | None | LEU2 | pFPP12/pFPP13 |
| pFPP55 | ARS415-CEN6 | CAS19 | CAS21 | CAS22 | LEU2 | pFPP13 |
| pFPP56 | ARS415-CEN6 | CAS19 | CAS21 | CAS22* | LEU2 | pFPP13 |

*reverse orientation

Various vectors or combinations of vectors were used to transform cells of the yeast *S. cerevisiae* (strain W303.1B).
These vectors and combinations of vectors are indicated in Table IV below.

TABLE IV

| Transformed strain | Parental strain | Vector 1 | Vector 2 | Vector 3 | Proteins expressed (§ indicates C-terminal fusion with an HA tag) | | | | | |
|---|---|---|---|---|---|---|---|---|---|---|
| | | | | | RbcS | RbcL | RbcX | GroES | GroEL | PRK |
| 11.19 | W303 | pCM185 | pFPP23 | pFPP19 | X§ | X | X§ | | | |
| 18.3 | W303 | pFPP45 | pFPP49 | | X | X | X | | | |
| 22.2 | W303 | pFPP45 | pFPP56 | | X | X | X | X | X | |
| 22.3 | W303 | pFPP45 | pFPP55 | | X | X | X | X | X | |
| 30.1 | W303 | pCM185 | | | | | | | | |
| 11.5 | W303 | pCM185 | pFL36 | pFPP5 | | | | | | |
| 11.7 | W303 | pCM185 | pFL36 | pFPP18 | X§ | X | | | | |
| 11.9 | W303 | pCM185 | pFL36 | pFPP19 | X§ | X | | | | |
| 11.15 | W303 | pCM185 | pFPP23 | pFPP5 | | | X§ | | | |
| 11.17 | W303 | pCM185 | pFPP23 | pFPP18 | X§ | X | X§ | | | |
| 14.5 | W303 | pFPP6 | | | | X§ | | | | |
| 14.12 | W303 | pFPP40 | | | | X§ | | | | |
| 14.6 | W303 | pFPP7 | | | X§ | | | | | |
| 14.7 | W303 | pFPP23 | | | | | X§ | | | |
| 16.3 | W303 | pFPP48 | | | | | X§ | | | |
| 16.5 | W303 | pFPP43 | pFPP23 | | X§ | X§ | X§ | | | |
| 16.6 | W303 | pFPP43 | | | X§ | X§ | | | | |
| yFB3 | CEN.PK | pFPP45 | pFPP20 | pFPP56 | X | X | X | X | X | X |

Notes:
pCM185: plasmid ATCC 87659;
pFL36: plasmid ATCC 77202

The transformed cells are grown at 30° C. in ambient air on YNB medium (yeast without nitrogen base supplemented with 6.7 g/l ammonium sulfate, 20 g/l glucose, 20 g/l agar for the agars) supplemented with commercial CSM medium (MP Biomedicals) suited to the selection markers of the plasmids used for the transformation. The cultures are stopped by cooling at 4° C. a generation before the end of the exponential phase.

An aliquot is taken from each culture and the cells are lysed with soda in the presence of SDS for analysis of total proteins on denaturing SDS gel.

The remainder of the cultures is centrifuged, then spheroplasts are prepared by enzymatic digestion of cell walls with a zymolyase-cytohelicase mixture in hypertonic sorbitol medium (1.2 M sorbitol). The spheroplasts are washed in hypertonic sorbitol medium in the presence of saturating concentrations of PMSF and EDTA (protease inhibitors), then broken by repeated pipetting and mild sonication in isotonic sorbitol medium (0.6 M). After centrifugation at low speed (1500 rpm) to remove large debris then at moderate speed (4000 rpm) to collect debris of intermediate sizes and mitochondria, the supernatant is collected and the proteins are precipitated at 80% saturation of ammonium sulfate with pH maintained at 6.5-7.0. The precipitate is redissolved and dialyzed in the presence of protease inhibitors, then fractionated by molecular sieving on a Sephacryl S300 column (GE Healthcare). The eluted fractions are combined in pools for gel analysis.

Total lysate and fractions sorted by molecular weights (native globular protein range of $10^4$ to $1.5 \times 10^6$ daltons) are analyzed on denaturing SDS-PAGE gel and nondenaturing gel (prestaining with Coomassie blue-PAGE). The gel is stained with Coomassie blue and the blot with Ponceau red for analysis of total proteins. RbcL, RbcS and RbcX proteins are detected after electrotransfer onto charged nylon by immunodetection. In the case of RbcL, detection can be carried out directly using an anti-RbcL antibody, and in the case of RbcS and RbcX, indirectly via an anti-HA-tag antibody. The various experiments were repeated while alternating co-expression of tag proteins or not in order to verify that the presence of the tags did not affect folding or assembly of the complexes.

FIG. 1 represents the analysis of total lysates of transformed strains.

The two subunits are expressed in yeast. RbcL is expressed at high level (visible by nonspecific staining of total proteins of an extract). The level of RbcS expression has not been quantified but appears similar to that of RbcL on the basis of anti-HA immunodetection. The two proteins exhibit no sign of degradation (absence of blurred or multiple bands) suggesting good folding quality and resistance to endogenous proteases. The chaperone RbcX is expressed as well and exhibits no sign of degradation. The plasmid systems for co-expressing the three components are operational and do not show notable interference with expression of the various components.

FIG. 2 represents the analysis by immunodetection of total lysate (box on the left of the Figure), and fractions sorted by molecular weight of strain 16.5, which co-expresses RbcL, RbcS, and RbcX, and its control, strain 16.3, which expresses RbcX.

Monomodal distribution of the RbcL subunit is observed within complexes 500 kDa or larger in size whereas the mass of the isolated subunit is 55 kDa. Distribution of RbcS and RbcX is on the contrary bimodal, one mode being of size similar to that observed for RbcL, the other corresponding to small sizes, close to those of isolated RbcS and RbcX proteins. Native RuBisCO complex is not convincingly visible with native gel and with nonspecific staining at the expected size (about 500 kDa) under these conditions. Nevertheless, a very large complex is detectable at about 750-1000 kDa (larger than the expected size) by immunodetection of RbcL.

FIG. 3 represents the results of the analysis on nondenaturing gel, followed by immunodetection using an anti-RbcL antibody, of total extracts of strains 11.9, 18.3 and 22.2, and fractions sorted by molecular weight of strain 22.2, which co-expresses RbcL, RbcS, and RbcX from *S. elongatus* and chaperones from *E. coli*. Then, in parallel, fractions sorted by molecular weight of strains 18.3 (on the left) and 22.2 (on the right).

These results show that co-expression with the chaperones GroES and GroEL induces a reduction in the size of the high molecular weight complex (about 750-1000 kDa) that was detected in the absence of these chaperones; in cells co-expressing RbcL, RbcS, RbcX, GroES and GroEL, a well-defined band corresponding to the expected size (about 500 kDa) for native RuBisCO complex is observed.

These results show that a prokaryotic form I RuBisCO complex can be expressed and correctly assembled in *S. cerevisiae* cells, this assembly being improved by the presence of the general chaperones GroES and GroEL.

For the analysis of RuBisCO activity in vitro, the extraction of soluble proteins of strain yFB3 is carried out. The cells are grown at 30° C. in ambient air on YNB (yeast without nitrogen base) medium, supplemented with 6.7 g/l ammonium sulfate, 20 g/l glucose, 20 g/l agar for the agars) with commercial CSM medium (MP Biomedicals), and suited to the selection markers of the plasmids used (medium without leucine, uracil and tryptophan for yFB3). The cultures are stopped by cooling at 4° C. a generation before the end of the exponential phase. The cultures are centrifuged, then spheroplasts are prepared by enzymatic digestion of cell walls with a zymolyase-cytohelicase mixture in hypertonic sorbitol medium (1.2 M sorbitol). The spheroplasts are washed in hypertonic sorbitol medium in the presence of 1 mM PMSF and EDTA (protease inhibitors), then broken by repeated pipetting and mild sonication in isotonic sorbitol medium (0.6 M). After centrifugation at low speed (200 g for 5 min) to remove large debris then at moderate speed (1500 g for 10 min) to collect debris of intermediate sizes and mitochondria, the supernatant is collected.

The tests for activity on the protein extracts are carried out in 50 mM TRIS/HCl (pH 7.5), 60 mM NaHCO$_3$ ($^{13}$C or $^{12}$C) 10 mM MgCl$_2$ in the presence of 2 mM ribulose diphosphate (RiDP) and 0.5 mg/ml total proteins of yFB3 extracts. At t=10 min and t=60 min, 100 µl of reaction mixture is taken, the reaction is stopped by adding 2 µl of HCl, and the sample is centrifuged for 10 min at 9300 g then analyzed by HPLC/MS (ion-pairing reversed-phase C18 with 10 mM tributylamine acetate/acetonitrile pH 6.0 gradient). Metabolites are detected by negative-ion electrospray mass spectrometry, and identified on the basis of their m/e ratios and elution times, compared with those of standard compounds.

The results are illustrated by FIG. 4.

In the presence of $^{13}CO_2$, the labeling ratio of 3-phosphoglycerate formed at 60 min is 52% as expected. Indeed, as represented at the bottom of FIG. 4, the reaction catalyzed by RuBisCO is the formation of two 3-phosphoglycerate molecules from one $CO_2$ molecule and one RiDP molecule. In the presence of $^{12}CO_2$, 3-phosphoglycerate is formed but only in its unlabeled form.

The RuBisCO present in the extracts is thus able to incorporate the carbon of $CO_2$ to produce 3-phosphoglycerate.

EXAMPLE 2: Phosphoribulokinase Expression in the Yeast *Saccharomyces cerevisiae*

Synthetic genes encoding five PRKs of different origin: *Synechococcus elongatus* (Syn), *Rhodobacter sphaeroides* (Rsph), *Rhodopseudomonas palustris* (Rpal), *Spinacia oleracea* (Sole), *Euglena gracilis* (Egra) and optimized for expression in yeast, and flanked or not flanked with a C-terminal HA tag, were prepared. The sequences of these synthetic genes (with no HA tag) are indicated in the appended sequence list under numbers SEQ ID NO: 4 to SEQ ID NO: 8, respectively.

Rsph and Rpal PRKs are class I PRKs existing in native form as an octamer for Rsph and as a hexamer for Rpal. Sole, Egra and Syn kinases are class II kinases whose native form is a dimer for the first two and a tetramer for the third.

The *Rhodobacter sphaeroides* (Rsph), *Rhodopseudomonas palustris* (Rpal), *Euglena gracilis* (Egra) and *Spinacia oleracea* (Sole) sequences were synthesized by the company Genecust and delivered in a pBlueScript II+ plasmid. The plasmids were amplified in the bacterium *Escherichia coli DH5α*. A maxiprep extraction is carried out for each plasmid. They are then digested with the enzymes BamHI and PstI then the digestion product is deposited on a 0.8% agarose gel containing SYBER Safe. Migration is carried out in 1×TAE buffer at 50 V for 30 minutes. Bands corresponding to open reading frames (972 bp for PRK from Rpal, 966 bp for Rsph, 1461 bp for Egra and 1277 bp for Sole) are cut out of the gel and DNA is extracted with the gel extraction kit from the company Fermentas. Lastly, the fragments are integrated into the vectors pCM185, pCM188-2 and pCM188-7 by ligation by ligase T4 (FERMENTAS) under the control of the doxycycline-repressible tetO promoter, to give the expression vectors pFPP20, pJLP1, pJLP2, pJLP3, pJLP4, respectively.

The cassettes and expression vectors thus obtained are listed in Table V below.

TABLE V

| Names | Origin type | Promoter | Terminator | Open reading frame | Markers | Host vector |
|---|---|---|---|---|---|---|
| pCM185 | ARS416-CEN4 | TetO7 | CYC1 | Ø | TRP1 | Ø |
| pCM188-2 | ARS416-CEN4 | TetO7 | CYC1 | Ø | URA3 | Ø |
| pCM188-7 | ARS416-CEN4 | TetO7 | CYC1 | Ø | URA3 | Ø |
| pFPP20 | ARS416-CEN4 | TetO7 | CYC1 | PRK *S. elongatus* | TRP1 | pCM185 |
| pFPP21 | ARS416-CEN4 | TetO2 | CYC1 | PRK *S. elongatus* | URA3 | pCM188-2 |
| pFPP22 | ARS416-CEN4 | TetO7 | CYC1 | PRK *S. elongatus* | URA3 | pCM188-7 |

TABLE V-continued

| Names | Origin type | Promoter | Terminator | Open reading frame | Markers | Host vector |
|---|---|---|---|---|---|---|
| pJLP1 | ARS416-CEN4 | TetO7 | CYC1 | PRK *E. gracilis* HA tag | TRP1 | pCM185 |
| pJLP2 | ARS416-CEN4 | TetO7 | CYC1 | PRK *R. sphaeroides* HA tag | TRP1 | pCM185 |
| pJLP3 | ARS416-CEN4 | TetO7 | CYC1 | PRK *R. palustris* HA tag | TRP1 | pCM185 |
| pJLP4 | ARS416-CEN4 | TetO7 | CYC1 | PRK *S. oleracea* HA tag | TRP1 | pCM185 |

These vectors were used to transform cells of *S. cerevisiae* strains W303.1B and CNPK. The first of these strains is a typical laboratory strain, the second is a semi-industrial strain.

The transformation was carried out according to the protocol of Chen et al. (Curr Genet. 1992, 21, 83-4), while maintaining at each transformation and subcloning step a doxycycline concentration of 2 µg/ml, suited to repression of the tetO promoter. The transformants were stored in glycerol-containing medium (50% glycerol) at −80° C. in the presence of 2 µg/ml doxycycline.

The transformed strains obtained are listed in Table VI below.

TABLE VI

| Transformed strain | Parental strain | Vector 1 | Vector 2 | Vector 3 | PRK expressed |
|---|---|---|---|---|---|
| 11.5 | W303 | pCM185 | pFL36 | pFPP5 | |
| 30.2 | W303 | pFPP20 | | | PRKsyn |
| 11.6 | W303 | pFPP20 | pFL36 | pFPP5 | PRKsyn |
| yJL1 | W303 | pJLP1 | | | PRK Egra |
| yJL2 | W303 | pJLP2 | | | PRK Rsph |
| yJL3 | W303 | pJLP3 | | | PRK Rpal |
| yJL4 | W303 | pJLP4 | | | PRK Sole |
| yJL5 | CENPK | pFPP20 | | | PRKsyn |
| yJL6 | CENPK | pJLP1 | | | PRK Egra |
| yJL7 | CENPK | pJLP2 | | | PRK Rsph |
| yJL8 | CENPK | pJLP3 | | | PRK Rpal |
| yJL9 | CENPK | pJLP4 | | | PRK Sole |

The transformed cells are put in preculture from the stock in YNB medium (yeast without nitrogen base supplemented with 6.7 g/l ammonium sulfate, 20 g/l glucose, 20 g/l agar for the agars) with commercial CSM medium (MP Biomedicals) suited to the support of plasmid selection and containing a concentration of 2 µg/ml doxycycline suited to the repression of PRK expression.

The influence of the expression of the various PRKs on cell viability was evaluated on agar medium in the presence or absence of doxycycline: Each strain is grown in liquid on selective CSM medium with 2 µg/ml doxycycline. An equivalent of 2 OD (OD at 600 nm) is collected then washed twice to remove the doxycycline. Tenfold dilutions are prepared. 10 µl of the dilutions is deposited in the form of drops (series of serial dilutions) of the cell suspensions, on agar plates (containing or not containing 2 µg/ml doxycycline) and incubated at 28° C. in normal atmosphere or alternatively in closed bags the atmosphere of which contains at least 90:10 (v/v) carbon dioxide/air.

The results in normal atmosphere are illustrated by FIG. 5. The results in $CO_2$-rich atmosphere are illustrated by FIG. 6.

It is noted that all the PRKs are more or less toxic in strain W3031B with high level of expression (induced). Nevertheless, toxicity appears much lower in strain CENPK, where only the Syn PRK is toxic in the induced state.

Other experiments show that in strain W303.1B, toxicity is strongly attenuated in an atmosphere poor in oxygen and rich in carbon dioxide.

The influence of the expression of the various PRKs on cell growth was evaluated on cultures in liquid medium: The strains are grown in selective CSM medium in closed tubes (containing or not containing 2 µg/ml doxycycline). Growth is monitored by measuring optical density at 600 nm until entry into stationary phase. For each strain, the relationship between the maximum growth rate µ (population increase per unit time) of the strain and that of the control strain (strain+empty plasmid) is determined.

The maximum growth rate µ ($µ_{max}$) ratios for each strain are illustrated by FIG. 7.

These results confirm that the toxicity of kinases in the context of strain CNPK 113-7D is lower than that of strain W303.1B.

A dose (induction level)-response (growth rate) toxicity effect is observed only for Sole kinase and in W303.1B.

In W303.1B, a significant toxicity of Rpal, Rsph, Syn kinases weakly and strongly expressed is observed. Toxicity appears lower for Egra kinase.

For the analysis of the metabolite ribulose-1,5 bisphosphate of the central carbon ring, the cells are washed to remove the doxycycline and placed in liquid culture at 30° C. on YNB (yeast without nitrogen base) medium supplemented with 6.7 g/l ammonium sulfate, 20 g/l glucose, (20 g/l agar for the agars) supplemented with commercial CSM medium (MP Biomedicals) suited to the selection marker of the plasmid used. The cultures are prepared in closed tubes with no oxygen supply beyond 3-10 volumes of air (not replenished) per volume of culture medium. Carbon dioxide stemming from the culture is thus maintained within the volume of the culture tube. This procedure limits the toxicity of the expression.

Metabolism is blocked by diluting the culture in 60:40 (v/v) methanol-water at −80° C. (mixture maintained at −40° C. in a dry ice/acetonitrile bath), followed by rapid centrifugation (temperature maintained below −20° C.) and cell lysis in a methanol-water (60:40 v/v) mixture containing 0.3 M soda then freezing at −80° C. according to the protocol described by Luo et al., (J. Chromatography A 1147:153-164, 2007).

After thawing, an aliquot is neutralized with glacial acetic acid, centrifuged, and the supernatant analyzed by HPLC/MS (ion-pairing reversed-phase C18 with tributylamine acetate/acetonitrile pH 6.0 gradient). Metabolites are detected by negative-ion electrospray mass spectrometry and identified on the basis of their m/e mass ratios and elution times, compared with those of standard compounds.

The results are illustrated by FIG. 8.

The activity level (not normalized to level of expression) estimated by the level of accumulation of ribulose-1,5-diphosphate produced from the reaction appears:

very high for Syn PRK even in repressed condition (50% of induced level). This activity is accompanied by toxicity with a significant drop in the level of intracellular ATP;

detectable but weaker for Egra and Sole PRKs in minimum medium;

undetectable under the conditions used for RspH and Rpai PRKs;

dependent on the culture medium, with for Syn PRK a level of ribulose-1,5-diphosphate accumulation much higher in poor medium than rich.

The whole of these observations indicates that only class II kinases lead to the accumulation of high levels of ribulose diphosphate in *S. cerevisiae*.

EXAMPLE 3: Phenotypic Characterization of Strains Containing the "Carboyeast" Engineering In Vitro by Study of the Functionality of Rubisco Complex Expressed in Yeast and Parameters Controlling Same As described in FIG. 4, the functionality of the artificial RuBisCO complex was shown in vitro by tests for RuBisCO activity on a synthetic substrate (ribulose diphosphate) from yeast extracts containing the complete or partial engineering, and by evaluating the appearance of the product of the reaction it catalyzes, namely 3-glycerophosphate.

3.1. Constructions and Strains Used

The present example was carried out using the constructions and transformed strains described in Tables VII to IX below.

TABLE VII

| | Expression cassettes | | | |
|---|---|---|---|---|
| Names | Promoter | Open reading frame | Tag | Terminator |
| CAS6 | TDH3p | RbcL *S. elongatus* optimized | None | ADH1t |
| CAS7 | TetO7p | PRK *S. elongates* optimized | None | CYC1t |
| CAS16 | TEF1p | RbcS *S. elongates* optimized | None | PGKt |
| CAS19 | TEF1p | RbcX *S. elongates* optimized | None | PGKt |
| CAS21 | PGI1p | GroES *E. coli* | None | CYC1t |
| CAS22 | TDH3p | GroEL *E. coli* | None | ADH1t |
| CAS23 | PGI1p | GroES *S. elongates* optimized | None | CYC1t |
| CAS25 | TDH3p | GroEL2 *S. elongates* optimized | None | ADH1t |
| CAS28 | PGI1p | polylinker | None | CYC1t |
| CAS33 | TEF1p | polylinker | None | PGKt |

TABLE VIII

| | Expression vectors (references to Table VII for the cassettes) | | | | | | |
|---|---|---|---|---|---|---|---|
| Names | Origin type | Cassette 1 | Cassette 2 | Cassette 3 | Auxotrophy markers | Host vector | *E. coli* replicon |
| pFPP13 | ARS415-CEN6 | CAS33 | None | None | LEU2 | pFL36 | Yes (AmpR) |
| pFFP53 | ARS415-CEN6 | CAS19 | CAS28 | None | LEU2 | pFL36 | Yes (AmpR) |
| pFFP56 | ARS415-CEN6 | CAS19 | CAS21 | CAS22* | LEU2 | pFL36 | Yes (AmpR) |
| pFB05 | ARS415-CEN6 | CAS19 | CAS25* | CAS21 | LEU2 | pFFP56 | Yes (AmpR) |
| pFB07 | ARS415-CEN6 | CAS23 | CAS22* | CAS19 | LEU2 | pFFP56 | Yes (AmpR) |
| pFB08 | ARS415-CEN6 | CAS23 | CAS25* | CAS19 | LEU2 | pFFP56 | Yes (AmpR) |
| pFB09 | ARS415-CEN6 | CAS21 | CAS22* | None | LEU2 | pFFP56 | Yes (AmpR) |
| pFPP45 | 2μ | CAS6 | CAS16 | None | URA3 | PYeDP51 | Yes (AmpR) |
| pFPP20 | ARS416-CEN4 | CAS7 | None | None | TRP | pCM185 | Yes (AmpR) |

*reverse orientation

TABLE IX

| Combination of plasmids and strains (references to Table VIII.) | | | | | | | | | | |
|---|---|---|---|---|---|---|---|---|---|---|
| Combination no. | Parental strain | Vector 1 | Vector 2 | Vector 3 | Proteins expressed | | | | | |
| | | | | | RbcS | RbcL | RbcX | PRKsyn | GroES | GroEL |
| 1b | CEN.PK 1605 | pYeDP51 | pCM185 | pFPP13 | | | | | | |
| 2 | CEN.PK 1605 | pFPP45 | pCM185 | pFPP56 | X | X | X | | coli | coli |
| 3 | CEN.PK 1605 | pFPP45 | pFPP20 | pFPP56 | X | X | X | syn | coli | coli |
| 4 | CEN.PK 1605 | pFPP45 | pFPP20 | pFPP53 | X | X | X | syn | | |
| 5 | CEN.PK 1605 | pFPP45 | pCM185 | pFPP53 | X | X | X | | | |
| 13b | CEN.PK 1605 | PYeDP51 | pCM185 | pFPP56 | | | | X | coli | coli |
| 15 | CEN.PK 1605 | PYeDP51 | pFPP20 | pFPP56 | | | | X | syn | coli | coli |

TABLE IX-continued

Combination of plasmids and strains (references to Table VIII.)

| Combination no. | Parental strain | Vector 1 | Vector 2 | Vector 3 | RbcS | RbcL | RbcX | PRKsyn | GroES | GroEL |
|---|---|---|---|---|---|---|---|---|---|---|
| 17b | CEN.PK 1605 | pFPP45 | pFPP20 | pFPP13 | X | X | | syn | | |
| 101 | CEN.PK 1605 | pFPP45 | pFPP20 | pFB08 | X | X | X | Syn | syn | L2 syn |

(Syn: *S. elongatus*; coli: *E. coli*; L2 syn: GroEL2 *S. elongatus*)

Notes:
1. pCM185: Commercial plasmid (ATCC 87659)
2. pFL36: Commercial plasmid (ATCC 77202)
3. PYeDP51: "Empty" plasmid, described in the following article: Urban P, Mignotte C, Kazmaier M, Delorme F, Pompom D. Cloning, yeast expression, and characterization of the coupling of two distantly related *Arabidopsis thaliana* NADPH-cytochrome P450 reductases with P450 CYP73A5. J Biol Chem. 1997 Aug. 1; 272(31):19176-86.
4. The other abbreviations refer to *S. cerevisiae* genes described in the data banks.
5. Synthetic genes: The *Synechococcus elongatus* genes encoding the chaperone specific to RuBisCO assembly (RbcX), as well as the general chaperones GroES, GroEL1 and GroEL2, were resynthesized after re-encoding for yeast implementing a proprietary inhomogeneous codon bias and cloned into pCC6301 (commercial).
6. *E. coli* chaperones GroES and GroEL were amplified from the bacterium, cloned into pSC-B-amp/kan (Stratagene) and assembled without re-encoding in the expression vectors (see Example 1).
7. The *Synechococcus elongatus* RbcS, RbcL, RbcX and PRK sequences were described in Examples 1 and 2.
8. The re-encoded sequences of cDNAs encoding *Synechococcus elongatus* chaperonins are described in the sequence listing (SEQ ID NO: 9 to 11) and inserted by homologous recombination in previously linearized vector pUC57 by co-transforming the two molecules in yeast. Similarly, the ORFs were amplified by PCR from previous constructions, generating flanking regions homologous to the promoters and terminators carried by vector pFPP56. That allowed cloning by homologous recombination by co-transforming this PCR product in a yeast strain with previously linearized vector pFPP56, generating the various expression vectors described in Table VIII according to the cassettes described in Table VII.

3.2. Evaluation of the Enzyme Activity of Synthetic RuBisCO Complex

For the extraction of soluble proteins of strains CEN.PK no. 3 and CEN-PK no. 4, the cells are grown at 30° C. in ambient air with shaking on YNB (yeast without nitrogen base) medium, supplemented with 6.7 g/l ammonium sulfate, 20 g/l glucose, 20 g/l agar for the agars, with commercial CSM medium (MP Biomedicals), suited to the selection markers of the plasmids used (medium without leucine, uracil and tryptophan). The cultures are stopped by cooling at 4° C. a generation before the end of the exponential phase.

The cultures are centrifuged, then spheroplasts are prepared by enzymatic digestion of cell walls with a zymolyase-cytohelicase mixture in hypertonic sorbitol medium (1.2 M sorbitol). The spheroplasts are washed in hypertonic sorbitol medium in the presence of 1 mM PMSF and EDTA (protease inhibitors), then broken by repeated pipetting and mild sonication in isotonic medium (0.6 M sorbitol). After centrifugation at low speed (200 g for 5 min) to remove large debris then at moderate speed (1500 g for 10 min) to collect debris of intermediate sizes and mitochondria, the supernatant is collected.

The tests for activity on the protein extracts are carried out in 50 mM TRIS/HCl (pH 7.5), 60 mM NaHCO$_2$, 10 mM MgCl$_2$ in the presence of 2 mM ribulose diphosphate (RiDP) and 0.05 mg/ml total proteins of the extracts. At various times, 60 μl of reaction mixture is taken, the reaction is stopped by adding 2 μl of HCl (12.1 M), and the sample is centrifuged for min at 9300 g then analyzed by HPLC/MS (ion-pairing reversed-phase C18 with 10 mM tributylamine acetate/acetonitrile pH 6.0 gradient). Metabolites are detected by negative-ion electrospray mass spectrometry and identified on the basis of their m/e ratios and elution times, compared with those of standard compounds.

The results are illustrated by FIG. 9. This Figure represents on the ordinate the number of moles of 3-phosphoglycerate detected (m/e of 185) obtained at various reaction times on the abscissa.

It is noted that for a complete engineering (CEN.PK no. 3: RbcS+RbcL+PRK+chaperones RbcX and GroES and GroEL from *E. coli*), referred to as the "CARBOYEAST" engineering, and a non-limiting substrate, the amount of product resulting from catalytic activity of the synthetic RuBisCO enzyme increases linearly in time. The RuBisCO complex expressed in yeast by the engineering is thus functional and stable.

It appears clearly that the association of the pair of general bacterial chaperones GroES GroEL with the chaperone RbcX, specialized in RuBisCO complex folding, is essential (FIG. 9 and Table X).

However, under the test conditions illustrated, co-expression of a combination of general bacterial chaperones (GroES and GroEL) from *E. coli*, associated with the specific chaperone RbcX from *S. elongatus*, is more effective for reconstructing functionality of the RuBisCO complex, itself from *S. elongatus*, than the same association but wherein all the elements come from the same organism, *S. elongatus* (Table X, lines 1 and 3).

TABLE X

Tests for RuBisCO activity in vitro carried out according to a protocol similar to that described before from extracts of CEN-PK strains grown on glucose and containing the engineering indicated in the first column. The tests are carried out during 80 min of incubation with 0.01-0.02 mg of protein of soluble extract of yeast in a reaction volume of 200 µl containing 2 mM ribulose diphosphate at room temperature. The activities are given in nmol of 3-phosphoglycerate formed/min/mg total proteins in the extract.

| Strains | | A | B | C |
|---|---|---|---|---|
| CEN.PK no. 3 | RbcS/RbcL/RbcX/PRK/(GroES/GroEL) E. coli | 20 | 13 | 20 |
| CEN.PK no. 2 | RbcS/RbcL/RbcX/(GroES/GroEL) E. coli | ND | 5 | 2.5 |
| CEN.PK no. 101 | RbcS/RbcL/RbcX/PRK/(GroES/GroEL2) S. elongatus | ND | ND | 1.5 |

3.3. Synthetic RuBisCO Incorporates $^{13}$C-Labeled $CO_2$ to Integrate Same in the Reaction Product The isotope incorporation experiment described above (FIG. 4) illustrates by quantification of labeled 3-glycerophosphate the capacity of the RuBisCO complex to produce labeled 3-glycerophosphate from ribulose diphosphate, by fixing carbon from $^{13}$C-labelled bicarbonate molecules.

3.4. RuBisCO Activity is Increased by the Presence of Carbonic Anhydrase

Carbonic anhydrase, by catalyzing the interconversion of bicarbonate to solvated carbon dioxide, is a known cofactor of the reaction. This example confirms the expected behavior for such a reaction. Interestingly, tests for activity in vitro show that adding bovine carbonic anhydrase in a final concentration of 10 µg/ml in the reaction volume of a test for RuBisCO activity, described above, increases the potential of the RuBisCO complex by a factor of three to four (FIG. 10). That suggests that optimization of the $CO_2$ concentration around the complex significantly increases the activities observed in the preceding test, which thus represents a minimal value for the reconstituted activities. Other factors could also contribute thereto in vivo; the measured values are thus only minimum values.

EXAMPLE 4: Phenotypic Characterization of Strains Containing the Engineering 4.1. Anaerobic Culture Shows an Increase in Ethanol Production Precultures were prepared on chemically defined medium. After thawing, 1 ml of a stock tube (−80° C.) was taken to inoculate a penicillin bottle (100 ml) containing 10 ml of culture medium (including 0.1 g/l formic acid supplemented with 20 g/l glucose), incubated for 18 hours at 30° C. and 120 rpm. The precultures were prepared in anaerobiosis (bottles previously flushed with nitrogen) and in the presence of doxycycline (2µ/ml) in order to avoid the toxicity problems observed in the presence of the PRK gene.

The precultures were then washed three times (centrifugation, resuspension, vortex for 15 s) with physiological saline (NaCl, 9 g/l), then the cell pellet was resuspended in culture medium without doxycycline.

These cells stemming from the precultures were then inoculated in order to reach an initial optical density of 0.05 (or 0.1 g/l). The starting culture volume was 50 ml in aerobiosis (250 ml baffled Erlenmeyer flasks) or 35 ml in anaerobiosis (100 ml penicillin bottles).

The cultures were stopped after all glucose was consumed or ethanol production stopped.

Anaerobic culture made it possible to characterize phenotypically strains containing the complete CARBOYEAST engineering or isolated elements, so as to characterize the influence of each on yeast.

FIG. 11 and Table XI show that, during anaerobic cultures on glucose, the complete CARBOYEAST engineering (RuBisCO_PRK Chaperones) or (RbcS+RbcL+PRK+RbcX+(GroES+GroEL) E. coli) induced an improvement in ethanol production, compared with an identical strain not integrating the Calvin cycle (RbcX+(GroES+GroEL) E. coli). The yield of ethanol produced from glucose consumed is thus improved by 7% (0.49 g/g vs. 0.46 g/g), to the detriment of biomass yield (0.035 vs. 0.051 g/g), suggesting marked redistribution of carbon toward ethanol production.

TABLE XI

Production yields of ethanol and biomass during anaerobic cultures (Prk: phosphoribulokinase)

| Genotype | | | Yields | |
|---|---|---|---|---|
| | | | Biomass | Ethanol |
| RuBisCO | PRK | Chaperones | g/g | g/g |
| − | − | + | 0.051 | 0.46 |
| + | + | + | 0.035 | 0.49 |

4.2. Study of RuBisCO Complex Functionality In Vivo

Experimental Protocol

Precultures were prepared on chemically defined medium. After thawing, 1 ml of a stock tube (−80° C.) was taken to inoculate a penicillin bottle (100 ml) containing 10 ml of culture medium (including 0.1 g/l formic acid supplemented with 20 g/l glucose), incubated for 18 hours at 30° C. and 120 rpm. The precultures were prepared in anaerobiosis (bottles previously flushed with nitrogen) and in the presence of doxycycline (2µ/ml) in order to avoid the toxicity problems observed in the presence of the PRK gene.

The precultures were then washed three times (centrifugation, resuspension, vortex for 15 s) with physiological saline (NaCl, 9 g/l), then the cell pellet was resuspended in culture medium without doxycycline.

These cells stemming from the precultures were then inoculated in culture medium containing 0.5 g/l formic acid and 0.5 g/l glucose. The starting culture volume was 25 ml (250 ml baffled Erlenmeyer flasks).

The various yeast strains are grown on $^{13}$C-labeled or unlabeled formate supplemented or not supplemented with unlabeled glucose. To demonstrate incorporation of the carbon isotope from formate, the isotopic composition of a stable cellular metabolite, ergosterol, is analyzed. The cell cultures were centrifuged for 5 min at 10000 rpm and the pellet resuspended in 7 ml of chloroform/methanol (2:1) and centrifuged for 5 min at 10000 rpm. The supernatant is supplemented with 2 ml of TE, and after centrifugation for 5 min at 10,000 rpm the chloroform phase is collected and evaporated under a stream of nitrogen. The residue is resuspended in 500 µl of methanol. The samples are analyzed by high-performance liquid chromatography (HPLC) on a chromatograph (Waters, Alliance 2690) equipped with an Aminex HPX 87-H$^+$ (300 mm×7.8 mm) column.

Results

As $CO_2$ transport in yeast from the outside to the inside of the cell is not a natural process, and awaiting a complementary engineering making it possible to establish same by co-expression of a transporter such as the specialized aquaporins described in S. elongatus, formic acid able to be oxidized by yeast dehydrogenase into carbon dioxide was used as intracellular carbon dioxide source. This carbon dioxide can potentially be reincorporated into organic materials through the RuBisCO complex. Thus, in the presence of $^{13}C$ labeled formate, incorporation of the isotope into biomass is expected. Nevertheless, the existence of other anaplerotic natural reactions (capable of fixing $CO_2$) in yeast explains why under these conditions one observes significant background noise from $^{13}C$ incorporation (about 3-4% of labeling) even in the absence of RuBisCO complex, making ambiguous the interpretation of the contribution of RuBisCO in the isotope incorporation observed. An analysis of metabolic pathways shows that the conditions used in this first experiment are in fact not suited to isotopic measurement of RuBisCO activity in vivo. It should be noted that this experiment made it possible nevertheless to confirm that the absence of incorporation in vivo of labeled bicarbonate when it is added to the culture medium using glucose and not formate as carbon source is indeed due to a problem of $CO_2$ (or bicarbonate/carbonate) transport and not to a metabolic problem.

Consequently, our attention is drawn to other evidence of proof of concept such as kinetics of formic acid consumption and maintenance of viability of strains carrying or not carrying the engineering. It should be noted that the use of formic acid as sole carbon source does not enable the strain to grow because of insufficient energy resources, at least in the absence of supplemental engineering of formate dehydrogenases. Only maintenance of viability is observable under these conditions. This energy balance can nevertheless be improved by adding a small amount of glucose.

Use of Formate as Carbon Source

Aerobic cultures on formic acid (0.45 g/l) and glucose (0.55 g/l) were used to characterize phenotypically strains containing the complete CARBOYEAST engineering or isolated elements so as to characterize growth on formic acid. Formic acid can be metabolized in yeast to $CO_2$ and reducing power ($H_2$) by formate dehydrogenase, nevertheless yeast is not able to grow on formic acid as sole carbon source.

FIG. 12 shows that, during aerobic cultures, the complete CARBOYEAST engineering (CEN.PK no. 3: RbcS+RbcL+PRK+RbcX+(GroES+GroEL) *E. coli*) induced complete consumption of formic acid, compared with an identical strain lacking PRK (CEN.PK no. 2: RbcS+RbcL+RbcX+(GroES+GroEL) *E. coli*), not allowing the production of substrate for RuBisCO. In parallel, an improvement in biomass production is observed, whereas glucose consumption remains identical. The strain having the complete engineering thus has a better capacity to transform formic acid.

4.3. Introduction in Yeast of a RuBisCO-Dependent Calvin Cycle Modifies In Vivo the Equilibrium of Biosynthetic Pathways in Central Metabolism The object of this study is to show that the introduction of a Calvin cycle in yeast by functional co-expression of RuBisCO (and chaperones) and phosphoribulokinase significantly modifies the internal metabolic profile in a direction compatible with the functionality of the engineering in vivo. This metabolic profile was evaluated after culture of strains carrying a complete or only partial engineering and comparative analysis of the phosphometabolome by mass spectrometry coupled to HPLC (ion-pairing reversed-phase chromatography).

The strains tested are: The strain containing the complete engineering (CEN.PK no. 3) and that lacking PRK (CEN.PK no. 2). The cells are grown at 30° C. in ambient air with shaking on YNB (yeast without nitrogen base) medium, supplemented with 6.7 g/l ammonium sulfate, 20 g/l glucose, 20 g/l agar for the agars) with commercial CSM medium (MP Biomedicals), and suited to the selection markers of the plasmids used (medium without leucine, uracil and tryptophan). The cultures are stopped by cooling at 4° C. a generation before the end of the exponential phase. The analysis is carried out on protein extractions stemming from 1 ml of cells in exponential growth phase quenched with 5 ml of 80% (v/v) methanol/water+10 mM $AcNH_4$. After centrifugation, the pellet is stored at -80° C. The extraction is carried out by suspending the pellet in 5 ml of 75% (v/v) ethanol/water, 10 mM $AcNH_4$ with extemporaneous addition of 150 µl of a mixture of pure metabolite standards labeled with $^{13}C$ (IDMS method). After incubation for 5 min at 80° C. and rapid cooling in a liquid nitrogen bath, centrifugation is used to remove the debris.

The IDMS method is used for absolute quantification. In the context of this analysis, absolute quantification of ribulose-1,5-bisphosphate could not be obtained due to the lack of availability of an adequate standard and was replaced by a non-isotopic external calibration which nevertheless allows an estimate (probably underestimated) of the concentration of this compound in yeast.

The results, presented in FIG. 13, suggest the re-equilibration of synthetic pathways within the cell taking into account the reconstituted Calvin cycle, which can be summarized by the metabolic simulation of FIG. 14.

The invention claimed is:

1. A transformed yeast cell, characterized in that it contains:
    a) an expression cassette containing a sequence encoding the RbcL subunit of a bacterial form I RuBisCO enzyme, under the transcriptional control of a suitable promoter;
    b) an expression cassette containing a sequence encoding the RbcS subunit of said RuBisCO enzyme, under the transcriptional control of a suitable promoter;
    c) an expression cassette containing a sequence encoding the specific chaperone RbcX of said RuBisCO enzyme, under the transcriptional control of a suitable promoter;
    d) an expression cassette containing a sequence encoding a general bacterial chaperone GroES, under the transcriptional control of a suitable promoter; and
    e) an expression cassette containing a sequence encoding a general bacterial chaperone GroEL, under the transcriptional control of a suitable promoter, wherein the RbcX originates from a different bacteria than the GroES and the GroEL.

2. The transformed yeast cell according to claim 1, characterized in that the GroES and GroEL originate-from *E. coli*.

3. The transformed yeast cell according to claim 1, characterized in that the chaperone RbcX is a cyanobacterial chaperone.

4. The transformed yeast cell according to claim 1, characterized in that GroES and GroEL come from a bacterium that does not naturally express a RuBisCO complex.

5. The transformed yeast cell according to claim 1, characterized in that the three expression cassettes mentioned in points c), d), and e) of claim 1 form a continuous block of genetic information.

6. The transformed yeast cell according to claim 1, characterized in that the expression cassettes mentioned in points c), d), and e) of claim 1 are carried by a single episomal genetic element.

7. The transformed yeast cell according to claim 1, characterized in that said yeast is *Saccharomyces cerevisiae*.

8. The transformed yeast cell according to claim 1, characterized in that the bacterial form I RuBisCO enzyme is a cyanobacterial RuBisCO enzyme.

9. The transformed yeast cell according to claim 8, characterized in that said cyanobacterium belongs to the genus *Synechococcus*.

10. The transformed yeast cell according to claim 1, characterized in that it further contains an expression cassette containing a sequence encoding a phosphoribulokinase (PRK) under the transcriptional control of a suitable promoter.

11. The transformed yeast cell according to claim 10, characterized in that said PRK is a class II PRK.

12. The transformed yeast cell according to claim 11, characterized in that said class II PRK is selected from PRKs from *Spinacia oleracea*, *Euglena gracilis*, or *Synechococcus elongatus*.

13. The transformed yeast cell according to claim 10, characterized in that the promoter controlling transcription of the sequence encoding the PRK is an inducible promoter.

14. The transformed yeast cell according to claim 2, characterized in that the chaperone RbcX is a cyanobacterial chaperone.

15. The transformed yeast cell according to claim 3, characterized in that the GroES and GroEL come from a bacterium that does not naturally express a RuBisCO complex.

16. The transformed yeast cell according to claim 2, characterized in that the three expression cassettes mentioned in points c), d), and e) of claim 1 form a continuous block of genetic information.

17. The transformed yeast cell according to claim 3, characterized in that the three expression cassettes mentioned in points c), d), and e) of claim 1 form a continuous block of genetic information.

18. The transformed yeast cell according to claim 4, characterized in that the three expression cassettes mentioned in points c), d), and e) of claim 1 form a continuous block of genetic information.

19. The transformed yeast cell according to claim 2, characterized in that the expression cassettes mentioned in points c), d), and e) of claim 1 are carried by a single episomal genetic element.

20. The transformed yeast cell according to claim 2, characterized in that the chaperone RbcX is a cyanobacterial chaperone.

21. The transformed yeast cell according to claim 20, characterized in that the GroES and GroEL come from a bacterium that does not naturally express a RuBisCO complex.

22. The transformed yeast cell according to claim 20, characterized in that the three expression cassettes mentioned in points c), d), and e) of claim 1 form a continuous block of genetic information.

23. The transformed yeast cell according to claim 1, further containing:

f) an expression cassette containing a sequence encoding a class II PRK under the transcriptional control of a suitable promoter, wherein the bacterial form I RuBisCO enzyme is a cyanobacterial RuBisCO enzyme and the GroES and GroEL are from *E. coli*.

* * * * *